(12) United States Patent
Jung et al.

(10) Patent No.: US 8,337,875 B2
(45) Date of Patent: Dec. 25, 2012

(54) CONTROLLING VESSEL GROWTH AND DIRECTIONALITY IN MAMMALS AND IMPLANTABLE MATERIAL

(75) Inventors: Steven B. Jung, Rolla, MO (US); Delbert E. Day, Rolla, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 12/683,211

(22) Filed: Jan. 6, 2010

(65) Prior Publication Data

US 2011/0014262 A1 Jan. 20, 2011

Related U.S. Application Data

(63) Continuation-in-part of application No. 12/504,489, filed on Jul. 16, 2009.

(51) Int. Cl.
A61F 2/00 (2006.01)
(52) U.S. Cl. ............................. 424/423
(58) Field of Classification Search ............ 424/400
See application file for complete search history.

(56) References Cited

U.S. PATENT DOCUMENTS

| | | | |
|---|---|---|---|
| 4,131,597 A | 10/1889 | Burleigh | |
| 4,512,038 A | 4/1985 | Alexander et al. | |
| 5,204,106 A | 4/1993 | Schepers et al. | |
| 5,691,256 A * | 11/1997 | Taguchi et al. | 501/63 |
| 6,447,805 B1 | 9/2002 | Healy | |
| 6,709,744 B1 | 3/2004 | Day et al. | |
| 7,338,517 B2 | 3/2008 | Yost et al. | |
| 7,811,954 B2 * | 10/2010 | Berthereau et al. | 501/36 |
| 2002/0160175 A1 | 10/2002 | Pirhonen | |
| 2004/0078077 A1 | 4/2004 | Binette et al. | |
| 2004/0170692 A1 | 9/2004 | Day et al. | |
| 2005/0021152 A1 | 1/2005 | Ogle et al. | |
| 2005/0102035 A1 | 5/2005 | Grundei | |
| 2005/0255159 A1 | 11/2005 | Hyers et al. | |
| 2006/0233887 A1 | 10/2006 | Day | |
| 2008/0066495 A1 | 3/2008 | Moimas et al. | |
| 2008/0208358 A1 | 8/2008 | Bellamkonda et al. | |
| 2009/0208428 A1 | 8/2009 | Hill et al. | |
| 2009/0276056 A1 | 11/2009 | Bose et al. | |

FOREIGN PATENT DOCUMENTS

| | | |
|---|---|---|
| EP | 1716873 A1 | 11/2006 |
| WO | 80/02378 A1 | 11/1980 |
| WO | WO 2007/124511 A2 * | 11/2007 |
| WO | 2007/144662 A1 | 12/2007 |

OTHER PUBLICATIONS

Kokubo et al., How useful is SBF in predicting in vivo bone activity?, 2006, Biomaterials 27 (2006) 2907-2915.*
Day, R.M., Bioactive Glass Stimulates the Secretion of Angiogenic Growth Factors and Angiogenesis in Vitro, 2005, Tissue Engineering, vol. 11, No. 5/6, pp. 768-777.*
Kokubo et al., How useful is SBF in predicting in vivo bone activity?, 2006, Biomaterials 27 (2006) pp. 2907-2915.*
Bunting et al., Bioresorbable Glass Fibres Facilitate Peripheral Nerve Regeneration, J. of Hand Surg. Eur. Vol. Jun. 2005 vol. 30 No. 3 242-247.*
Hesaraki et al., Montmorillonite-added calcium phosphate bioceramic foams, Key Engineering Materials vols. 361-363(2008), pp. 111-114.*
Gafni et al. (Tissue Eng. Nov. 2006;12(11):3021-34).*
Anderson et al. (J Histochem Cytochem. Aug. 2004;52(8):1063-72).*
Day et al. (J Biomed Mater Res A. Dec. 15, 2005;75(4):778-87).*
Kim et al. (Adv. Funct. Mater. 2006, 16, 1529-1535).*
Pezzatini et al. (Bone 41 (2007) 523-534).*
Rahaman et al. (Advances in Bioceramics and Biocomposites; The American Ceramic Society; 2005).*
Neel et al. (Biomaterials 26 (2005) 2247-2254).*
Hosseinkhani et al. (Biomaterials vol. 27, Issue 34, Dec. 2006, pp. 5836-5844).*
Keshaw et al. (Biomaterials vol. 26, Issue 19, Jul. 2005, pp. 4171-4179).*
Yao, Aihua et al., "In Vitro Bioactive Characteristics of Borate-Based Glasses with Controllable Degradation Behavior", Journal of the American Ceramic Society, vol. 90 Issue 1, Nov. 7, 2006, pp. 303-306.
Ning, Jia et al., "Synthesis and in Vitro Bioactivity of a Borate-Based Bioglass", Materials Letters, vol. 61, Issue 30, Dec. 2007, pp. 5223-5226.
Liang, Wen, "Bioactive Comparison of a Borate, Phosphate and Silicate Glass", Journal of Materials Research, vol. 21, Issue 1, 2005, pp. 125-131.
Jung, Steven, "Conversion Kinetics of Silicate, Borosilicate, and Borate Bioactive Glasses to Hydroxyapatite", Physics and Chemistry of Glasses—European Journal of Glass Science and Technology Part B, Apr. 2009, vol. 50, No. 2, pp. 85-88.
Liang, Wen et al., "Bioactive Borate Glass Scaffold for Bone Tissue Engineering", Journal of Non-Crystalline Solids, Journal of Non-Crystalline Solids, vol. 354, Issues 15-16, Mar. 15, 2008, pp. 1690-1696.
Li et al., "An Investigation of Bioactive Glass Powders by Sol-Gel Processing," [online abstract], Journal of Applied Biomaterials, 1991, vol. 2, Issue 4, pp. 231-239.
"A New Generation of Bioactive Materials Useful for Bone and Tissue Repair," Missouri University of Science and Technology, Sep. 13, 2010, <http://www.ibridgenetwork.org/file_records/show/8512>.
International Search Report, PCTUS2010/041835, dated Sep. 17, 2010, 4 pages.
Written Opinion, PCTUS2010/041835, dated Sep. 17, 2010, 6 pages.
Liu et al., "Bioactive borosilicate glass scaffolds: improvement on the strength of glass-based scaffolds for tissue engineering", Journal of Material Science: Materials in Medicine, vol. 20, No. 1, Sep. 2008, pp. 365-372.
Rahaman et al., "Preparation and Bioactive Characteristics of Porous Borate Glass Substrates", Ceramic Engineering and Science Proceedings, vol. 26, No. 6, 2005, pp. 3-10.
Yao et al., "Preparation of Bioactive Glasses with Controllable Degradation Behavior and their Bioactive Characterization", Chinese Science Bulletin, vol. 52, No. 2, Jan. 2007, pp. 272-276.

(Continued)

Primary Examiner — David J Blanchard
Assistant Examiner — Devang Thakor
(74) Attorney, Agent, or Firm — Senniger Powers LLP

(57) ABSTRACT

A method for directing vessel growth toward a blood-deficient site in a mammal comprising implanting into the mammal an assembly of at glass fibers to form a vascular bridge with a first end of the vascular bridge in contact with the blood-deficient site and a second end of the vascular bridge remote from the blood-deficient site. Over time the bridge biodegrades and promotes vascularity in the direction of the bridge.

33 Claims, 14 Drawing Sheets

OTHER PUBLICATIONS

Huang et al., "Strength of Hollow Hydroxyapatite Microspheres Prepared by a Glass Conversion Process", Journal of Materials Science: Materials in Medicine, vol. 20, No. 1, Aug. 14, 2008, pp. 123-129.

Carmeliet et al., "Common mechanisms of nerve and blood vessel wiring", Nature, vol. 436, Jul. 14, 2005, pp. 193-200.

International Preliminary Report on Patentability, PCT/US2010/041835, dated Jan. 17, 2012, 8 pages.

* cited by examiner

←——————— Fiber Orientation ———————→

25μm

Reacted Fibers

Soft Tissue

CONTROLLING VESSEL GROWTH AND DIRECTIONALITY IN MAMMALS AND IMPLANTABLE MATERIAL

REFERENCE TO RELATED APPLICATION

This application is a continuation-in-part of U.S. application Ser. No. 12/504,489 filed Jul. 16, 2009.

STATEMENT OF GOVERNMENT INTEREST

This invention was made with Government support under Department of the Army contract W81XWH-08-1-7065. The Government may have certain rights in the invention.

FIELD OF THE INVENTION

This invention relates to directing vessel growth in mammals by surface and subsurface implantation of a biocompatible and biodegradable material into mammalian hosts.

BACKGROUND OF THE INVENTION

Patent application publication WO 80/02378 discloses a carrier manufactured from an absorbable plastic, ethylene/vinyl acetate, collagen, or albumin material for promoting vascularization and endothelial activity in mammals. The carrier is in the form of a tube, sheet, thread, or net, and can, for example, be laid over skin ulcers.

U.S. Pat. No. 4,512,038; U.S. Pat. App. Pub. 2004/0078077; U.S. Pat. App. Pub. 2008/0208358; U.S. Pat. App. Pub. 2004/0267362; U.S. Pat. No. 7,338,517; and EP 0 469 070 disclose various polymeric and other fiber-based implantable scaffolds to facilitate tissue repair in mammals.

Silicate-based glasses have been used as a basis for implantable compositions to support the bonding, growth or genesis of bone by fostering a supportive environment between the material and living, bone progenitor cells. It is widely recognized that successful bioactive glasses include silica and calcia in order to foster the needed supportive environment. Certain of these compositions are considered bioactive since they possess surfaces capable of fostering a calcium phosphate layer which, in turn, promotes bone bonding to the material. For example, U.S. Pat. No. 5,204,106 discloses a composition termed 45S5 glass which contains $Na_2O$—$CaO$—$P_2O_5$—$SiO_2$.

Day et al. U.S. Pat. No. 6,709,744 describes biocompatible materials for implantation which include borate-based glass or ceramic materials containing $Na_2O$, $CaO$, $P_2O_5$, and $B_2O_3$. A specific example is a glass containing about 22.9 wt % $Na_2O$, about 22.9 wt % CaO, about 5.6 wt % $P_2O_5$, and about 48.6 wt % $B_2O_3$. These materials contain a high CaO concentration to facilitate the formation of hydroxyapatite when exposed to phosphorus-containing fluids in-vivo or prior to implantation. These materials are in the form of loose particulates which are loosely packed, for example in a glass capillary tube for release into a host. Liang et al., Bioactive Borate Glass Scaffold for Bone Tissue Engineering, J. Non-Crystalline Solids 354 (2008), p. 1690-96; and Yao et al., In-Vitro Bioactive Characteristics of Borate-Based Glasses with Controllable Degradation Behavior, J. Am. Cer. Soc. 90 (2007), p. 303-306 also disclose borate-based glasses formulated with high CaO to facilitate such formation of hydroxyapatite. For example, the 0B, 1B, 2B, and 3B glasses described by Yao et al. contain 0, 17.7, 35.4, and 53 wt % $B_2O_3$.

There is a continuing need for biocompatible materials which promote vessel growth in the repair of wounds, ulcers, sores, severe burns, and other injuries at a site of compromised blood flow requiring enhance blood flow for healing.

SUMMARY OF THE INVENTION

Briefly, therefore, the invention is directed to a method for directing vessel growth toward a blood-deficient site in a mammal comprising implanting into the mammal an assembly of at least about 5 individual glass fibers to form a vascular bridge with a first end of the vascular bridge in contact with the blood-deficient site and a second end of the vascular bridge remote from the blood-deficient site and proximate a blood-rich site; wherein each fiber has a length:diameter aspect ratio of greater than 10:1; wherein the length from the first end of the vascular bridge to the second end of the vascular bridge is at least about 1 millimeter; wherein an aspect ratio of the length to cross section of the bridge at least about 7.5:1; and wherein said fibers comprise biocompatible glass fibers which biodegrade in physiological fluids and comprise at least one glass-former selected from the group consisting of $P_2O_5$, $SiO_2$, $B_2O_3$, and combinations thereof.

In another aspect, the invention is a vascular bridge comprising at least about 5 individual glass fibers wherein each fiber has a length:diameter aspect ratio of greater than 10:1; wherein the length from the first end of the vascular bridge to the second end of the vascular bridge is at least about 1 millimeter; wherein an aspect ratio of the length to cross section of the bridge at least about 7.5:1; and wherein said fibers comprise biocompatible glass fibers which biodegrade in physiological fluids and comprise at least one glass-former selected from the group consisting of $P_2O_5$, $SiO_2$, $B_2O_3$, and combinations thereof.

Other objects and features of the invention are in part apparent and in part pointed out hereinafter.

DESCRIPTION OF PREFERRED EMBODIMENTS

Figure 1:
FIG. 1 is a photograph of a vascular bridge of the invention during implantation.

In accordance with this invention, a biologically compatible and biodegradable inorganic material is implanted as a vascular bridge into a mammal, which material chemically reacts with physiological fluids in a way that promotes growth of bodily tissue specifically by increasing the number of blood vessels. In particular, the material reacts in the host to form a biologically useful material which over time is absorbed into the body and is replaced by new tissue. New blood vessels grow along the length of the bridge, thus facilitating the delivery of blood flow to a blood-deficient site in the host. This method of increasing vascularity is used to treat blood-deficient sites in mammals (such as wounds, ulcers, sores, and severe burns) which require additional blood flow for healing. The material is in the form of a generally longitudinal assembly of components of the material which is implanted into the mammal as a vascular bridge with a first end of the bridge in contact with the blood-deficient site and a second end of the bridge remote from the blood-deficient site and in contact with a blood-rich site. As the assembly biodegrades, vascularity increases along the assembly, vessel growth is directed, and blood flow is increased to the blood-deficient site.

In some embodiments the fibers comprise a calcium-containing biocompatible glass which upon dissolution in physiological fluids leaves a track comprising a calcium-containing compound from the second end to the first end of the bridge to support blood vessel growth from the second end to the first end. In other embodiments the vascular bridge upon dissolution in physiological fluids leaves a track comprising a porous hollow tube from the second end to the first end to support blood vessel growth from the second end to the first end.

The assembly of biocompatible, biodegradable materials employed as a vascular bridge in connection with this invention comprises longitudinal fibers of glass material, which in accordance with this description encompasses both glass and glass/ceramic material. Generally speaking, the vascular bridge comprises fibers each having a length of at least about 1 mm, such as at least about 3 mm. For example, the assembly includes fibers having a length of at least about 3 mm, such as at least about 5 mm, such as at least about 10 mm, or even in some instances at least about 20 mm. The length of the fibers is dictated by the application for which they are being used, and may be up to 1000 mm or more. In some embodiments the length of the fibers is less than about 150 mm, such as less than about 100 mm, or less than about 50 mm.

Each fiber has a diameter which is less than about 50 µm in one embodiment, such as between about 20 and about 50 µm (microns). In a different embodiment, each fiber has a diameter between about 50 µm and about 450 µm, for example, between about 100 and about 450 µm, such as between about 100 and about 300 µm.

The length to diameter aspect ratio of the fibers employed in this invention is at least 2:1, typically at least 5:1, and even more typically at least about 10:1, such as from about 10:1 to about 1000:1. In some alternative embodiments, this aspect ratio is on the order of at least about 1500:1, e.g., from 1500:1 to about 10,000:1. In one example, the fibers have a length of about 30,000 µm (30 mm) and a diameter of about 20 µm, which corresponds to a length to cross-section aspect ratio of the individual fibers of about 1500:1. The cross-section is typically circular and the cross-sectional dimension a diameter. But it is not critical that the cross section be strictly circular, as the fibers may be ellipsoidal, flat, rectangular, triangular, or other shape in cross section. So the term "diameter" is used loosely herein and includes the largest dimension of non-circular cross-sections.

The number of fibers in the assembly is typically at least about 5, and more typically between about 10 and about 10000 or more fibers, such as between about 50 and about 500 fibers. There are various embodiments, such as embodiments having between about 100 and about 300 fibers, and embodiments having between about 200 and about 800 fibers. The aspect ratio of the length to cross section of the overall assemblage is preferably at least about 7.5:1, such as at least about 50:1.

In one embodiment, the implantable material is a loose assemblage of several or more fibers generally co-aligned as the vascular bridge shown in FIG. 1. This photo shows an assemblage of about 200 fibers each having a length of about 30,000 µm and a total bridge diameter of about 4000 µm, during subcutaneous implantation into the back of mammalian host, here a rat. In FIG. 1 the bridge is being shown implanted perpendicular to the axis of the rat's spine. The aspect ratio of the length to cross section of the overall assemblage is about 7.5:1. In this embodiment, the fibers are in the form of a loose assemblage in that they are not bonded together. Inasmuch as bonding of the fibers imparts brittleness to the overall assemblage, unbonded fibers are preferred in many embodiments because they tend to remain more flexible and less prone to breakage during implantation and natural movement of the host.

Figure 2:
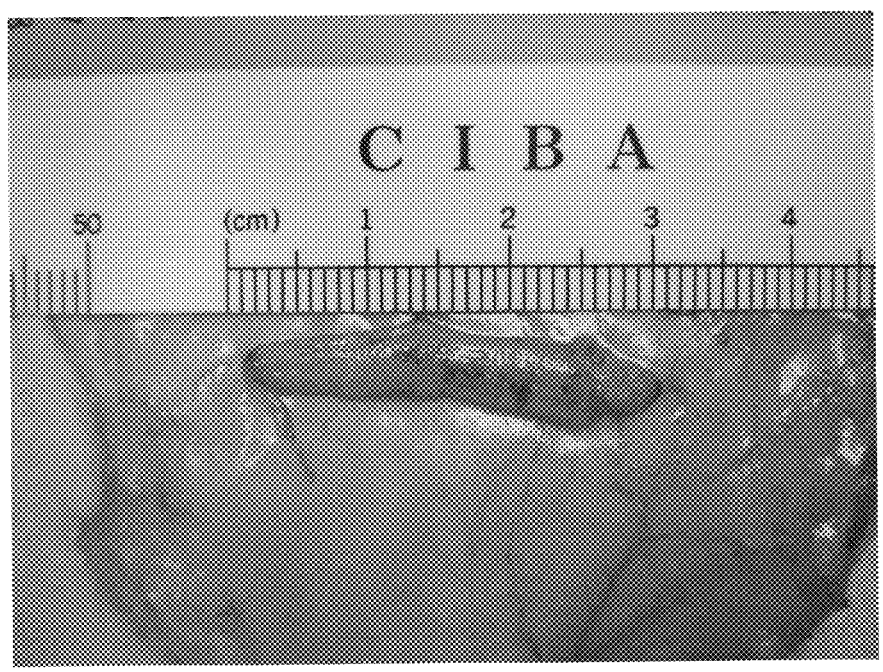
FIGS. 2 and 3 are photographs of a vascular bridge of the invention after implantation and removal from a host.
Figure 3:
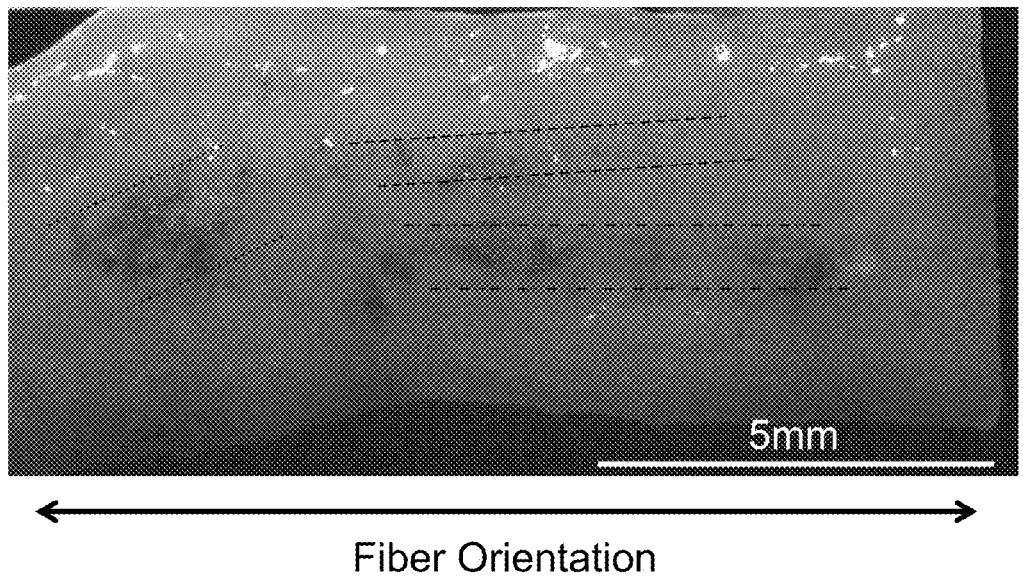

FIG. 2 is a photograph of the vascular bridge of FIG. 1 two weeks after implantation. It can be seen in this photo that vascularity has been promoted as new blood vessels which are visible as the dark spots on the vascular bridge. FIG. 3 shows a segment of the 30 mm long vascular bridge two weeks after implantation, with superimposed dotted lines indicating the longitudinal orientation of vessel growth. This orientation of vascular growth, shown between the pairs of dashed lines, corresponds generally to the orientation of the vascular bridge indicated by the solid line underneath the photo in FIG. 3. FIGS. 2 and 3 therefore show that vessel growth is promoted along the length of the bridge, which delivers blood flow from one end of the bridge to the other.

As an alternative to the embodiment shown in FIGS. 1 to 3 where the vascular bridge is a loose assembly of unbonded components, alternatively the fibers are bonded to each other, typically by heating, to define a vascular bridge having a compressive strength of greater than 0.4 MPa. The desired compressive strength is selected so that the components are in no sense free flowing, and so that the bridge body can be handled without disintegrating into the individual body components. The desired compressive strength is also selected to provide the strength that is required to remain integral after implantation. In some preferred embodiments, the compressive strength of the bridge is at least about 5 MPa, while in other embodiments where greater rigidity is required, the compressive strength is at least about 20 MPa, such as between about 20 and about 200 MPa.

The initial surface area of the vascular bridge varies depending on morphology such as whether it is all fibers, the fiber dimensions, etc. Moreover, the surface area changes during biodegradation. Generally speaking, a vascular bridge according to some embodiments of the invention has a surface area/bulk vascular bridge volume of between about 1 and about 1000 $cm^{-1}$, such as between about 50 and about 500 $cm^{-1}$.

In accordance with one embodiment of this invention, a trace element such as B, Cu, F, Fe, Mn, Mo, Ni, Si, Sr, and Zn, and in some particularly preferred embodiments, Cu, Sr, Zn, and/or Fe, is optionally incorporated into the material of the implantable vascular bridge. These elements have a beneficial effect on endothelial cell migration which can be useful for blood vessel formation and have importance for tissue regeneration. In this way, these trace elements promote angiogenesis, which is a critical function in promoting tissue growth, such as in wound healing. This is in distinction from promoting osteoconductivity, which refers to providing bone growth factors to a site to promote bone growth. Angiogenesis, which involves increasing vascularity, i.e., vessel growth, is distinct from osteoconductivity.

In those instances when the one or more trace elements are employed, they are incorporated into the implantable material in a concentration of at least about 0.05 wt %, or at least about 0.1 wt %. In most instances, the concentration is less than 10 wt %, or less than 5 wt %, such as between about 0.05 and about 5 wt %, for example between about 0.1 and about 2.5 wt % (per element). Where the implantable biocompatible material is borate-based or phosphate-based, the trace element concentration is less than 5 wt %, and it may be higher and up to 10 wt % where the biocompatible material is silicate-based. The trace elements are selected from the group consisting of B, Cu, F, Fe, Mn, Mo, Ni, Si, Sr, and Zn. In certain preferred embodiments the trace element is one or more selected from the group consisting of Cu, F, Fe, Mn, Mo, Sr, and Zn. In some especially preferred embodiments for certain applications, the trace element is one or more selected from the group consisting of Cu, Fe, Sr, and Zn. More than one of these trace elements can be employed in a single composition. Silicon as a trace element is applicable to borate-based and phosphate-based glasses, and not to silicate-based glasses. Boron as a trace element is applicable to silicate-based and phosphate-based glasses, and not to borate-based glasses. Accordingly, the group of Cu, F, Fe, Mn, Mo, Sr, and Zn has more general applicability. Also, certain of these elements may be present in greater amounts in that they are not being used as trace elements in accordance with this invention. For example, a scaffold made of a biocompatible glass material which contains 0.4 wt % Cu and 15 wt % Sr contains Cu as a trace element in accordance with this invention; and it contains Sr, but not as a trace element in accordance with this invention. Such a material would indeed satisfy the requirement herein for a trace element from the group Cu, F, Fe, Mn, Mo, Ni, Sr, and Zn in a concentration between about 0.05 and 10 wt % by virtue of the material's Cu content, regardless of its unqualifying Sr content.

Where Cu is desired, the source of Cu to the glass or partially crystalline biocompatible vascular bridge material may be a copper oxide such as CuO or $Cu_2O$ or other copper compounds such as copper nitrate or copper sulfate, for example. In one embodiment, Cu is incorporated into the vascular bridge in a concentration of between about 0.05 and about 5 wt % (about 0.06-6 wt % CuO; about 0.055-5.5 wt % $Cu_2O$), such as between about 0.1 and about 2.5 wt % (about 0.12-3 wt % CuO; about 0.11-3 wt % $Cu_2O$). There are preferred embodiments employing from about 1 wt % to about 2 wt % Cu, as provided by between about 1.2 wt % and about 2.4 wt % CuO.

Where Sr is desired, the source of Sr to the glass or partially crystalline biocompatible vascular bridge material may be an oxide such as SrO or other Sr compounds such as $SrCO_3$, for example. In one embodiment, Sr is incorporated into the vascular bridge in a concentration of between about 0.05 and about 5 wt % (about 0.06 to 5.90 wt % SrO), such as between about 0.1 and about 2.5 wt % (about 0.12 to 2.95 wt % SrO). There are preferred embodiments employing from about 1 wt % to about 2 wt % Sr, as provided by between about 1.18 wt % and about 2.36 wt % SrO.

Where Zn is desired, the source of Zn to the glass or partially crystalline biocompatible material may be an oxide such as ZnO or other Zn compounds such as $Zn_3(PO_4)_2$-$xH_2O$, for example. In one embodiment, Zn is incorporated into the glass in a concentration of between about 0.05 and about 5 wt % (about 0.06 to 6.0 wt % ZnO), such as between about 0.1 and about 2.5 wt % (about 0.12 to 3.0 wt % ZnO). There are preferred embodiments employing from about 1 wt % to about 2 wt % Zn, as provided by between about 1.20 wt % and about 2.40 wt % ZnO.

Where Fe is desired, the source of Fe to the glass or partially crystalline biocompatible material may be an oxide such as FeO, $Fe_3O_4$, $Fe_2O_3$, or other Fe compounds such as $FeSO_4$-$7H_2O$, for example. In one embodiment, Fe is incorporated into the glass in a concentration of between about 0.05 and about 5 wt % (about 0.06 to 6.45 wt % FeO), such as between about 0.1 and about 2.5 wt % (about 0.13 to 3.23 wt % FeO). There are preferred embodiments employing from about 1 wt % to about 2 wt % Fe, as provided by between about 1.29 wt % and about 2.58 wt % FeO.

The glass formers in certain embodiments of the invention are concentration balanced to impart the desired biodegradability. For example, in one embodiment, the concentrations of the glass formers borate, silicate, and phosphate are balanced to 52.95 wt %, 0 wt %, and 4.0 wt %, respectively, with respect to themselves and with respect to the other components in the material $Na_2O$, CaO, and $K_2O$. Balancing in this regard encompasses balancing the concentration of one glass former with other components, such as with those glasses which contain borate and other components, but no phosphate or silicate.

In many preferred embodiments of the vascular bridge, the concentrations of glass formers are balanced such that at least about 20 wt % of the biocompatible vascular bridge material biodegrades within six weeks of implantation in its mammalian host. For example, the concentrations of glass formers are balanced such that at least about 20 wt % of the biocompatible vascular bridge material biodegrades within six weeks of implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these scaffolds are implanted into the subcutaneous sites of rats, on average at least 20 wt % of the scaffolds' material biodegrades within six weeks; and in at least 68% of rats at least 15 wt % of the scaffold biodegrades; and in at least 90% of rats at least 10 wt % of the scaffold degrades. Implantation for this and the following standards is according to the protocol described below in Example 1. Biodegrading in most instances manifests itself either as vascular bridge weight loss, but can also manifest itself as another reaction of the vascular bridge material involving a change of state which results in release of trace element into the host.

Similarly, in another aspect, the concentrations of glass formers are balanced such that at least about 20 wt % of the trace element concentration in the vascular bridge is released from the scaffold into the host within six weeks of implantation in its mammalian host. For example, the concentrations of glass formers are balanced such that at least about 20 wt % of the trace element concentration in the vascular bridge is released from the scaffold into the host within six weeks of implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these vascular bridges are implanted into the subcutaneous sites of rats, on average at least 20 wt % of the scaffolds' trace element concentration is released within six weeks; and in at least 68% of rats at least 15 wt % of the vascular bridge trace element concentration is released; and in at least 90% of rats at least 10 wt % of the vascular bridge trace element concentration is released.

On the other hand, the vascular bridge does not biodegrade so quickly in the host that it fails to provide trace elements over a long enough period to adequately promote angiogenesis. For example, at least 50 wt % of the vascular bridge material remains for at least two weeks and does not biodegrade within two weeks. That is, the concentrations of glass formers are balanced such that at least about 50 wt % of the biocompatible vascular bridge material remains for at least two weeks after implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these vascular bridges are implanted into the rats, on average at least 50 wt % of the vascular bridge material does not biodegrade within two weeks; and in at least 68% of rats at least 37.5 wt % of the vascular bridge does not biodegrade within two weeks; and in at least 90% of rats at least 25 wt % of the vascular bridge does not biodegrade within two weeks.

Moreover, in these embodiments, at least 50 wt % of the vascular bridge trace element concentration remains for at least two weeks. That is, the concentrations of glass formers are balanced such that at least about 50 wt % of the trace element remains for at least two weeks after implantation in a Fisher 344 rat having an age between 9 and 11 weeks and a weight between 200 and 300 grams. In accord with this measure, the testing is performed on rats with a standard deviation of 25% (relative) of the biocompatible vascular bridge material and a population size of 10. In other words, when 10 of these vascular bridges are implanted into the rats, on average at least 50 wt % of the vascular bridge trace element concentration remains for at least two weeks; and in at least 68% of rats at least 37.5 wt % of the vascular bridge trace element concentration remains for at least two weeks; and in at least 90% of rats at least 25 wt % of the vascular bridge trace element concentration remains for at least two weeks.

In one embodiment of the invention the biocompatible vascular bridge releases the trace element at particular rate of release of trace element, per gram of glass, per day in a mammalian host. The release rate can in effect be "dialed in" by determining the desired amount of trace element to be released within the host, and then selecting a biocompatible composition or combination of compositions to achieve this rate. As noted above, the glass formers are concentration balanced to impart the desired biodegradability. In a related aspect, the surface area per unit volume can be used to control release rate, as greater surface area increases reactivity and therefore release rate. One skilled in the art appreciates that the rate of biodegradation of the vascular bridge material is different from host to host, from glass to glass, from trace element to trace element, and otherwise depends on a number of factors. For example, a more physically active host with a faster average heart rate may encourage biodegradation and therefore trace element release at a faster rate. In one embodiment, the composition has a trace element release (Cu) rate of between about 0.5 and about 100 E-7 moles of trace element, per gram of glass, per day; for example, between about 1 and about 25 E-7 moles of trace element, per gram of glass, per day; such as between about 1 and about 20 E-7 moles of trace element, per gram of glass, per day, or between about 3 and about 12 E-7 moles of trace element, per gram of glass, per day.

As an alternative perspective on trace element release for this invention, in one embodiment for certain applications, the rate of release is between about 0.1 and about 60 micromolar; i.e., between about 0.1 and about 60 micromoles trace element are released per liter of flow through the vascular bridge. In other embodiments, the composition is formulated to provide a release rate of between about 0.5 and about 30 micromolar, such as between about 3 and about 12 micromolar. For example, in one embodiment where the trace element is Cu and the composition is a borate-based or silicate-based scaffold, the vascular bridge is prepared to yield a Cu release rate during blood flow therethrough of between about 0.1 and about 60 micromolar, such as between about 0.5 and 30 micromolar, or between about 3 and about 12 micromolar.

As noted above, the biocompatible materials of the inventive vascular bridges biodegrade in physiological fluids. However, in comparison to articles characterized as "water soluble" which dissolve relatively rapidly (over a period of, e.g., 24 hours) in aqueous solutions, the biocompatible materials of the invention are not water soluble, that is, they are resistant to rapid water solubility. For example, vascular bridges made from them having a surface area and size of practical application for use as an implantable vascular bridge do not completely dissolve in a less than several weeks (e.g., six weeks) at 37° C. in an aqueous phosphate solution or an aqueous solution with a miscible solvent such as methanol, ethanol, isopropanol, acetone, ethers or the like. As understood in the art, materials which are "water soluble" are subject to relatively rapid solubility; and materials which are "water insoluble" are either entirely insoluble in water, or are at least only dissolvable with difficulty. Generally speaking the vascular bridge materials are not water insoluble and are not water soluble under this characterization; rather, they are of intermediate water solubility.

The material of the vascular bridge is biocompatible in that it is not toxic or otherwise harmful to its host's living tissue. Some of the preferred compositions (Ca-free) of the invention are also not bioactive, in the sense that hydroxyapatite does not form. That is, they lack bioactivity, where bioactivity refers to a material's capacity in phosphorus-containing mammalian fluids to foster growth of a calcium phosphate layer or convert to bone-precursor calcium phosphate compounds which, in turn, promotes bone bonding to the material.

In one embodiment the biocompatible material for the vascular bridge is a borate-based glass material containing the following, approximately, with all percentages herein being by weight, unless stated otherwise:

| | |
|---|---|
| $B_2O_3$ | 40 to 80 |
| $Na_2O$ | 0 to 25 |
| $Li_2O$ | 0 to 25 |
| $K_2O$ | 0 to 25 |
| $Rb_2O$ | 0 to 25 |
| CaO | 0 to 40 |
| MgO | 0 to 25 |
| SrO | 0 to 40 |
| BaO | 0 to 50 |
| $Li_2O + Na_2O + K_2O + Rb_2O$ | 0 to 50 cumulative |
| MgO + SrO + BaO + CaO | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

The concentrations of $K_2O$ and MgO in certain of these embodiments are each from about 1 to about 25 wt %. In most embodiments, the one or more of $Li_2O$, $Na_2O$, $K_2O$, and $Rb_2O$ is present in a cumulative concentration between about 1 and about 50 wt %, such as between about 5 and about 20 wt %; and the one or more of MgO, SrO, BaO, and CaO is present in a cumulative concentration between about 1 and about 50 wt %, such as between about 5 and about 40 wt %. Where Cu is an optionally included trace element, this composition further contains 0.05 to 5; or 0.01 to 2.5 wt % Cu; as CuO, Cu$_2$O, or other Cu compound. The transition metal elements are those elements where the d-band contains less than its maximum number of ten electrons per atom, and includes, among others, Co and Ni. In fact, certain of the trace elements used in accordance with this invention such as Zn and Fe are transition metals. So in formulations where the trace element concentration of these trace elements is stated to be in a particular range such as between about 0.1 and about 2.5 wt %, of course the trace element concentration is in that range regardless of the fact that transition elements may be among the trace elements, and if Zn and Fe are present in an amount greater than 2.5 wt %, they are not trace elements.

A few exemplary glass materials of the invention are as follows:

TABLE 1

Trace-Element-Containing Borate Biocompatible Glasses (wt %)

| Glass | B$_2$O$_3$ | Na$_2$O | CaO | K$_2$O | MgO | P$_2$O$_5$ | CuO | SrO | ZnO | Fe$_2$O$_3$ |
|---|---|---|---|---|---|---|---|---|---|---|
| 1 | 52.95 | 5.99 | 19.98 | 11.99 | 5.00 | 4.00 | 0.10 | | | |
| 2 | 52.89 | 5.99 | 19.96 | 11.98 | 4.99 | 3.99 | 0.20 | | | |
| 3 | 52.79 | 5.98 | 19.92 | 11.95 | 4.98 | 3.98 | 0.40 | | | |
| 4 | 52.47 | 5.94 | 19.80 | 11.88 | 4.95 | 3.96 | 1.00 | | | |
| 5 | 51.94 | 5.88 | 19.60 | 11.76 | 4.90 | 3.92 | 2.00 | | | |
| 6 | 51.73 | 5.86 | 19.52 | 11.71 | 4.88 | 3.90 | 0.40 | 2.00 | | |
| 7 | 51.20 | 5.80 | 19.32 | 11.59 | 4.83 | 3.86 | 0.40 | 2.00 | 1.00 | |
| 8 | 50.88 | 5.76 | 19.20 | 11.52 | 4.80 | 3.84 | 0.40 | 2.00 | 1.00 | 0.40 |

In most embodiments the biocompatible vascular bridge material consists only or essentially of components meeting these compositional requirements or other narrower descriptions herein. But generally speaking, for some embodiments other materials not meeting these descriptions may be incorporated into the vascular bridge. In some embodiments the vascular bridge comprises fibers of a first composition and fibers of a second composition different from the first composition. The bridge may also comprise a mixture of fibers of more than two distinct compositions.

Additional borate-based materials within this description, into which Cu or other stated trace element may be incorporated according to this invention, contain, by weight %, the following, keeping in mind that one or more of the other trace elements may be included in addition to Cu in analogous concentrations, or instead of Cu:

TABLE 2

Wt. % Composition of Additional Borate Glasses

| | B$_2$O$_3$ | Na$_2$O | K$_2$O | Li$_2$O | CaO | BaO | MgO | P$_2$O$_5$ | CuO |
|---|---|---|---|---|---|---|---|---|---|
| A | 52.5 | 6.0 | 12.0 | | 20.0 | | 5.0 | 4.0 | 0.5 |
| B | 70.3 | | | 10.3 | 19.3 | | | | 0.1 |
| C | 63.7 | 19.0 | | | 17.2 | | | | 0.1 |
| D | 49.0 | 14.6 | | | | 36.0 | | | 0.4 |
| E | 78.4 | | | 11.5 | 10.0 | | | | 0.1 |
| F | 69.9 | | | 10.0 | 10.0 | 10.0 | | | 0.1 |
| G | 78.6 | | | 11.3 | | | 10.0 | | 0.1 |
| H | 78.6 | | | 11.3 | | 10.0 | | | 0.1 |
| I | 75.9 | | | 11.0 | | 13.0 | | | 0.1 |
| J | 58.6 | | | 8.0 | | 33.0 | | | 0.4 |

It can therefore be appreciated that in addition to the Cu, and/or in addition to Sr, Zn, Fe, Mn, F, Si, Ni, and/or Mo, the borate-based biocompatible vascular bridge materials include 40 to 80 wt % B$_2$O$_3$ or 50 to 80 wt % B$_2$O$_3$, or even the narrower B$_2$O$_3$ ranges described herein, in combination with 1 to 25 wt % Na$_2$O, 1 to 25% K$_2$O, 1 to 40 wt % CaO, 1 to 25 wt % MgO, and 1 to 10 wt % P$_2$O$_5$. Or the component materials may contain 40 to 80 wt % B$_2$O$_3$, 1 to 25 wt % Li$_2$O, and 1 to 40 wt % CaO. Or they may contain 40 to 80 wt % B$_2$O$_3$, 1 to 25 wt % Na$_2$O, and 1 to 40 wt % CaO. Or they may contain 40 to 80 wt % B$_2$O$_3$, 1 to 25 wt % Na$_2$O, and 1 to 40 wt % BaO. Or they may contain 40 to 80 wt % B$_2$O$_3$, 1 to 25 wt % Li$_2$O, and 1 to 25 wt % MgO. Or they may contain 40 to 80 wt % B$_2$O$_3$, 1 to 25 wt % Li$_2$O, and 1 to 40 wt % BaO. While the biocompatible materials hereinabove and hereinbelow are described as containing various oxides by weight %, those skilled in the art understand that in the final glass or glass/crystalline composition, the oxide compounds are dissociated, and the specific oxides, e.g., B$_2$O$_3$, SiO$_2$, P$_2$O$_5$, etc. are not separately identifiable or even necessarily separately present. Nonetheless, it is conventional in the art to refer to the final composition as containing a given % of the individual oxides, so that is done here. So from this perspective, the compositions herein are on an equivalent basis.

The biocompatible materials of the invention containing the trace element in certain preferred versions are borate-based in that they contain between about 40 and about 80 wt % B$_2$O$_3$, such as between about 50 and about 80 wt % B$_2$O$_3$. Borate-based materials have several important advantages for biological use such as their ease of preparation, ability to be made into glass particulates, microspheres or fibers at relatively low temperatures without crystallization, and, particularly, their biocompatibility. The borate-based materials disclosed herein, compared to silicate-based materials, have significantly faster reaction rates, lower melting temperatures, resistance to crystallization, and in certain instances the absence of silica, which only slowly degrades in the body. So while certain embodiments employ up to about 18 wt % SiO$_2$ in many other preferred embodiments herein, the materials are silicate-free, containing less than 0.1 wt % silicate or even no silicate. Borate glasses in many instances form hollow fibers upon reaction in-vivo, while silicate glasses do not; and they facilitate angiogenesis in-vivo. The borate materials described herein also release boron in-vivo as they react with the body fluids.

There is one embodiment which has specific preference in certain applications and wherein the concentration of Ca (elemental or in CaO or other compounds) in the vascular bridge material is controlled to less than about 5 wt %. Certain preferred embodiments strictly control the Ca concentration to less than about 0.5 wt %, such as to less than 0.2 wt %, and even to less than 0.1 wt %. The advantage in this embodiment to strictly controlling Ca concentration is the avoidance of the formation of calcium phosphate compounds, apatite type compounds, and related amorphous calcium phosphate (ACP) upon exposure to physiological phosphorus-containing fluids. Such apatite compounds include hydroxyapatite $Ca_5(PO_4)_3(OH)$, fluoroapatite $Ca_5(PO_4)_3F$, amorphous calcium phosphate (ACP), and other calcium-containing compounds. Thus, in certain applications it is advantageous to avoid the formation of Ca-apatite compounds because they have a relatively lower radiopacity than do, for example, analogous Sr or Ba compounds. In certain situations it is advantageous to avoid Ca-apatite compounds in order to form compounds which degrade more rapidly, or perhaps even more slowly. It can also be advantageous to avoid Ca for purposes of controlling melt characteristics, such as viscosity, melting temperature, and/or crystallization tendency. The Ca-free compositions lack bioactivity, where bioactivity refers to a material's capacity in phosphorus-containing mammalian fluids to foster growth of a calcium phosphate layer or convert to bone-precursor calcium phosphate compounds.

The biocompatible Ca-free material employed for certain embodiments of the bridge preferably contains between about 40 and about 90 wt % $B_2O_3$ with the remainder being selected from alkali oxides and alkaline earth oxides, and other optional constituents listed below. For example, this material contains, by weight %:

| | |
|---|---|
| $B_2O_3$ | 40 to 80 |
| $Na_2O$ | 0 to 25 |
| $Li_2O$ | 0 to 25 |
| $K_2O$ | 0 to 25 |
| $Rb_2O$ | 0 to 25 |
| MgO | 0 to 25 |
| SrO | 0 to 40 |
| BaO | 0 to 25 |
| $Li_2O + Na_2O + K_2O + Rb_2O$ | 0 to 50 cumulative |
| MgO + SrO + BaO | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

In addition, the material optionally contains Cu in a concentration of 0.05 to 5; or 0.01 to 2.5 wt %, as CuO, $Cu_2O$, or other Cu compound, and/or other trace element. Certain of these embodiments contain low levels of Ca, as described above; while others are substantially Ca-free and contain essentially no or less than 0.1 wt % Ca.

In one preferred embodiment, the vascular bridge material contains between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; and between about 5 and about 40% alkaline earth component selected from the group consisting of MgO, SrO, BaO, and combinations thereof. Optional components include $P_2O_5$, $SiO_2$, $Al_2O_3$, F, and transition metal elements. Lanthanides are specifically and strictly excluded from certain preferred embodiments. In some embodiments the biocompatible material consists essentially of between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; between about 5 and about 40 wt % alkaline earth component selected from the group consisting of MgO, SrO, BaO, and combinations thereof, and between about 0.05 and 5 wt % Cu, as CuO, $Cu_2O$, or other Cu compound Exemplary borate-based Ca-free materials, into which Cu may be incorporated according to this invention, contain, by weight %, the following, keeping in mind that one or more of the other trace elements may be included in addition to Cu in analogous concentrations, or instead of Cu:

TABLE 3

Wt. % Composition of Ca-Free Borate Glasses

| | $B_2O_3$ | $Na_2O$ | $Li_2O$ | MgO | BaO | CuO |
|---|---|---|---|---|---|---|
| I | 49.0 | 14.6 | | | 36.1 | 0.3 |
| II | 78.7 | | 11.1 | 10.0 | | 0.2 |
| III | 78.7 | | 11.1 | | 10.0 | 0.2 |
| IV | 75.8 | | 11.0 | | 13.0 | 0.2 |
| V | 58.7 | | 8.0 | | 33.0 | 0.3 |
| VI | 45.0 | | 6.6 | | 48.0 | 0.4 |
| VII | 69.7 | | 10.0 | 10.0 | 10.0 | 0.3 |

In certain embodiments of the invention, the biocompatible material is selected to include at least two of the alkali oxides $Li_2O$, $Na_2O$, $K_2O$, and/or $Rb_2O$ in a cumulative concentration of between about 5 and about 25 wt %, such as between about 8 and 20 wt %. It has been discovered to be advantageous to include two or more such alkali compounds in order to reduce the tendency for crystallization, which ultimately improves the workability and manufacturability of the glasses, which can important to making bridges. Using more than one type of alkali (i.e., mixed alkali) can reduce the cost of a glass, modify its reaction rate with body fluids, and provide additional elements beneficial to tissue growth and regeneration.

A further feature of certain embodiments is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %. If SrO is present in a concentration which yields a Sr concentration above 10 wt %, it does not qualify as a trace element in accordance with this description.

These embodiments into which Cu and/or other trace element may be incorporated and which employ mixed alkali oxide contents contain $B_2O_3$ from about 40 to about 80 wt %. Certain of these embodiments consist essentially of $B_2O_3$ from about 40 to about 80 wt %, mixed alkali oxides selected from the group consisting of $Li_2O$, $Na_2O$, $K_2O$, and $Rb_2O$, and one of MgO, SrO, BaO, or CaO, plus the Cu or other trace element compound. Other embodiments consist essentially of $B_2O_3$ from about 40 to about 80 wt %, two or more alkali oxides selected from the group consisting of $Li_2O$, $Na_2O$, $K_2O$, and $Rb_2O$, and two or more alkaline earth oxides from the group consisting of MgO, SrO, BaO, and CaO, plus the Cu or other trace element compound. For example, composition A in Table 2 consists essentially of $B_2O_3$ from about 40 to about 80 wt %, two or more mixed alkali oxides selected from the group consisting of $Li_2O$, $Na_2O$, $K_2O$, and $Rb_2O$ in a cumulative wt % between 5 and 25%, and two or more from among MgO, SrO, BaO, and CaO in a cumulative wt % between 8 and 25%. Other embodiments optionally include one or more of $P_2O_5$, $SiO_2$, $Al_2O_3$, F, and transition metal elements.

The invention includes forming a bridge from biocompatible materials with an especially high $B_2O_3$ composition, namely, from about 60 to about 82 wt %, preferably from about 70 to about 80 wt %. These embodiments employ an alkali oxide selected from the group consisting of $Li_2O$, $Na_2O$, $K_2O$, $Rb_2O$, and combinations thereof cumulatively from about 1 to about 50 wt %, such as from about 5 to about 25 wt %, and even from about 8 to about 20 wt %; and even optionally two or more such oxides cumulatively in this range. They also optionally employ alkaline earth oxides from group consisting of MgO, SrO, BaO, CaO, and combinations thereof in the range of about 1 to about 50 wt %, such as in the range of 1 to 30 wt %, or even about 8 to 25 wt %, and even two or more such oxides cumulatively in this range. Certain of these embodiments consist essentially of these components, such as compositions II, III, IV, and VII in Table 3; while other embodiments optionally include one or more of $P_2O_5$, $SiO_2$, $Al_2O_3$, F, and transition metal elements.

In the foregoing described mixed-alkali and high-borate embodiments, the Ca concentration may be strictly controlled to less than about 5 wt %, including to less than 0.5 wt %, such as to less than 0.2 wt % or less than 0.1 wt % to avoid the formation of Ca compounds, in the manner discussed above. Alternatively, there are embodiments containing two or more alkali oxides which also contain CaO in an amount up to about 40 wt % to facilitate the formation of hydroxyapatite, other calcium phosphate compounds, or amorphous calcium phosphate.

Some exemplary materials of the invention contain, approximately, 40 to 80 wt % $B_2O_3$, 0.05 to 5% CuO, and $Na_2O$, $K_2O$, MgO, and $P_2O_5$. More specific examples contain or even consist essentially of 40 to 90 wt % $B_2O_3$, 0.1 to 5% CuO, 1 to 25 wt % $Na_{20}$, 1 to 25 wt % $K_2O$, 1 to 25 wt % MgO, and 1 to 10 wt % $P_2O_5$.

The invention also encompasses bridges formed from a phosphate-based or silicate-based material which is at least partially dissolvable in mammalian bodily fluids, and Cu is optionally incorporated into the biocompatible material in a concentration as described above. In these embodiments, $P_2O_5$ and/or $SiO_2$ are glass formers and constitute about 20 to about 65 wt % $P_2O_5$ or about 20 to about 60 wt % $SiO_2$. These materials also contain an alkali metal oxide component of, for example, one or more of $Li_2O$, $Na_2O$, $K_2O$, $Rb_2O$, $Cs_2O$, or a mixture thereof in a concentration of about 8 wt % to about 55 wt %, such as about 10 to about 52 wt %. Many of these phosphate- and silicate-based glasses also contain a calcium component, one of CaO, $CaF_2$, or mixtures thereof. For example, many of these glasses contain from about 5 to about 40 wt % of CaO or $CaF_2$, or mixtures thereof, such as about 10 to about 30 wt % of CaO or $CaF_2$, or mixtures thereof, or about 10 to about 15 wt % of CaO or $CaF_2$, or mixtures thereof. Accordingly, one of these embodiments contains about 20 to about 65 wt % $P_2O_5$, and one or more of $Li_2O$, $Na_2O$, $K_2O$, $Rb_2O$, $Cs_2O$, or a mixture thereof in a concentration of about 8 wt % to about 55 wt %, and a calcium component in a concentration of about 5 to about 40 wt % of CaO or Ca $F_2$, and optionally Cu or other trace element in a concentration of about 0.05 to about 5 wt %, such as between about 0.1 and about 2.5%. Another embodiment contains about 20 to about 65 wt % $P_2O_5$, and one or more of $Li_2O$, $Na_2O$, $K_2O$, $Rb_2O$, $Cs_2O$, or a mixture thereof in a concentration of about 10 wt % to about 52 wt %, a calcium component of CaO or $CaF_2$ or mixtures thereof in a concentration of about 5 wt % to about 40 wt % of CaO or $CaF_2$ or mixtures thereof, and Cu or other trace element in a concentration of about 0.05 to about 5 wt %, such as between about 0.1 and about 2.5%. Another embodiment contains about 20 to about 65 wt % $P_2O_5$, and one or more of $Li_2O$, $Na_2O$, $K_2O$, $Rb_2O$, $Cs_2O$, or a mixture thereof in a concentration of about 8 wt % to about 55 wt %, a calcium component of CaO or $CaF_2$ or mixtures thereof in a concentration of about 10 to about 30 wt % of CaO or $CaF_2$ or mixtures thereof, and Cu or other trace element in a concentration of about 0.05 to about 5 wt %, such as between about 0.1 and about 2.5%. Another of these embodiments contains about 20 to about 60 wt % $SiO_2$, and one or more of $Li_2O$, $Na_2O$, $K_2O$, $Rb_2O$, $Cs_2O$, or a mixture thereof in a concentration of about 8 wt % to about 55 wt %, a calcium component of CaO in a concentration of about 5 to about 40 wt % of CaO or $CaF_2$, and Cu or other trace element in a concentration of about 0.05 to about 5 wt %, such as between about 0.1 and about 2.5 wt %. Another embodiment contains about 20 to about 60 wt % $SiO_2$, and one or more of $Li_2O$, $Na_2O$, $K_2O$, $Rb_2O$, $Cs_2O$, or a mixture thereof in a concentration of about 10 wt % to about 52 wt %, a calcium component of CaO or $CaF_2$ or mixtures thereof in a concentration of about 5 wt % to about 40 wt % of CaO or $CaF_2$ or mixtures thereof, and optionally Cu or other trace element in a concentration of about 0.05 to about 5 wt %, such as between about 0.1 and about 2.5 wt %. Another embodiment contains about 20 to about 60 wt % $SiO_2$, and one or more of $Li_2O$, $Na_2O$, $K_2O$, $Rb_2O$, $Cs_2O$, or a mixture thereof in a concentration of about 8 wt % to about 55 wt %, a calcium component of CaO or $CaF_2$ or mixtures thereof in a concentration of about 10 to about 30 wt % of CaO or $CaF_2$ or mixtures thereof, and optionally Cu or other trace element in a concentration of about 0.05 to about 5 wt %, such as between about 0.1 and about 2.5 wt %. In certain of these embodiments, $CaF_2$ is strictly avoided and the calcium component is CaO.

Examples of silicate-based biocompatible material containing Cu and other trace elements in accordance with this invention are as follows:

TABLE 4

Weight Percent Composition of Silicate-Based Biocompatible Glasses (wt %)

| Glass | $SiO_2$ | $Na_2O$ | $P_2O_5$ | CaO | CuO | FeO | $CaF_2$ | $B_2O_3$ | ZnO | MnO | MgO | $K_2O$ |
|---|---|---|---|---|---|---|---|---|---|---|---|---|
| A | 44.6 | 24.3 | 5.9 | 24.3 | 1.0 | | | | | | | |
| B | 44.1 | 24.0 | 5.9 | 24.0 | 2.0 | | | | | | | |
| C | 43.7 | 23.8 | 5.8 | 23.8 | 3.0 | | | | | | | |
| D | 43.2 | 23.5 | 5.8 | 23.5 | 4.0 | | | | | | | |
| E | 42.8 | 23.3 | 5.7 | 23.3 | 5.0 | | | | | | | |
| F | 44.0 | 25.0 | 6.0 | 20.0 | 0.2 | 0.2 | 1.0 | 2.2 | 0.6 | 0.2 | 0.6 | |
| G | 50.0 | 6.0 | | 19.0 | 0.2 | 0.2 | 1.0 | 3.0 | 1.0 | 0.2 | | 12.0 |

Examples of phosphate-based biocompatible glass contain Cu in accordance with this invention are shown in Table 5.

TABLE 5

Weight Percent Composition of Phosphate-Based Biocompatible Glasses

| Glass ID | $Na_2O$ | $K_2O$ | CaO | MgO | $B_2O_3$ | $P_2O_5$ | $Li_2O$ | SrO | CuO |
|---|---|---|---|---|---|---|---|---|---|
| P-1 | 3.8 | 5.8 | 27.5 | 2.5 | 0.0 | 60.0 | 0.0 | 0.0 | 0.4 |
| P-2 | 9.2 | 9.3 | 27.5 | 0.0 | 0.0 | 53.5 | 0.0 | 0.0 | 0.5 |
| P-3 | 7.8 | 11.8 | 17.0 | 7.6 | 0.0 | 55.2 | 0.0 | 0.0 | 0.6 |
| P-4 | 7.8 | 11.8 | 17.0 | 7.6 | 0.0 | 55.2 | 0.0 | 0.0 | 0.6 |

TABLE 5-continued

Weight Percent Composition of Phosphate-Based Biocompatible Glasses

| Glass ID | Na$_2$O | K$_2$O | CaO | MgO | B$_2$O$_3$ | P$_2$O$_5$ | Li$_2$O | SrO | CuO |
|---|---|---|---|---|---|---|---|---|---|
| P-5 | 6.6 | 8.9 | 21.9 | 0.0 | 4.1 | 58.0 | 0.0 | 0.0 | 0.5 |
| P-6 | 10.5 | 0.0 | 23.0 | 0.0 | 4.0 | 61.1 | 1.1 | 0.0 | 0.3 |
| P-7 | 8.0 | 3.7 | 1.5 | 0.0 | 1.8 | 78.1 | 0.0 | 6.7 | 0.2 |

These phosphate-based formulations demonstrate situations where it is advantageous to include at least two of the alkali oxides Li$_2$O, Na$_2$O, K$_2$O, and/or Rb$_2$O in a cumulative concentration of between about 5 and about 25 wt %, such as between about 8 and 20 wt %. As noted above, it has been discovered to be advantageous to include two or more such alkali compounds in order to reduce the tendency for crystallization, which ultimately improves the workability and manufacturability of the glasses, which can be important to making vascular bridges. Using more than one type of alkali (i.e., mixed alkali) can reduce the cost of a glass, modify its reaction rate with body fluids, and provide additional elements beneficial to tissue growth and regeneration.

A further feature of these phosphate-based embodiments is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %.

In certain embodiments of the invention, the vascular bridge may optionally contain glass of one or more non-fibrous morphologies selected from the group consisting of beads, particles, ribbons, hollow spheres, and flakes. Generally speaking, these shapes have a diameter of at least about 10 μm, such as between about 10 μm and about 500 μm.

There is also an option with this invention of employing distinct component compositions to strategically impart certain properties. For example, the vascular bridge composition in some embodiments employs 10 to 90 wt % of components having one composition selected from the above, and 10 to 90 wt % of components of a different composition. Or even more than two such types of components may be employed. That is, the material may contain at least 10 wt % of components comprising a first component material within the contemplated compositions and at least 10 wt % of components comprising a second component material, wherein the first and second component materials have compositions distinct from each other. And it is contemplated that only the first component material may contain Cu and/or other trace element. This permits the selection of, for example, faster reacting fibers in combination with slower reacting fibers; or the selection of Ca-containing fibers with Ca-free fibers. One can therefore select standard composition components and combine them with non-standard composition components to effectively customize or dope the bridge for the application presented, or for the host's particular needs. Alternatively, hollow spheres containing a growth factor or drug for delivery to the host can be incorporated with the fibers of the vascular bridge.

The vascular bridge is formed to have an open or interconnected porosity which is sufficient to provide fluid flow thru to facilitate uptake of bodily fluids, while maintaining sufficient strength for handling and implantation. The porosity is between about 15 vol % and about 90 vol %. There are different levels of porosity, for example between about 15 and about 30 vol %, or between about 30 and about 60 vol %, or between about 60 and about 90%, which are preferred for different applications. Porosity depends on or is controlled by many factors such as fiber orientation, shape of particles or microspheres, and any thermal treatment (time/temperature) optionally employed to bond the elements together. Independent of this bulk porosity, interconnectivity is also important in the various embodiments of the invention. Because vessel growth is strongly influenced by the flow of bodily fluids into the bridge, it is preferred to have a high level of interconnected pores within the bridge, and a low level of closed pores. That is, it is important that most pores be connected to other pores, and that there is a direct or indirect path from most pores to the exterior surface of the bridge. In certain embodiments, at least about 80 vol %, such as at least about 90%, of the pore volume of the bridge is directly or indirectly through other pores accessible from the bridge exterior, and therefore accessible to bodily fluids.

The method of making the biocompatible materials is not narrowly critical to the invention. By way of example, in preparing the biocompatible materials, individual analytical reagent grade components are weighed, mixed thoroughly, and melted in a platinum crucible at temperatures ranging from 900 to 1500° C. for approximately one to four hours. The melt is then quenched, for example, on a steel or copper plate to form glass that can be ground into particulates of a desired size. The material of preferred compositions when in the form of a melt can easily be formed into fibers. Fibers can either be pulled by hand directly from the melt or pulled through bushing by a rotating drum.

The bridge is prepared by placing and orienting fibers in a generally unidirectional or co-aligned manner. If bonding is desired, the fibers are place in a mold and heated to a temperature where the fibers soften and bond together. In one preferred embodiment, the fibers are self bonded in the sense that no adhesive, braze, or other external bonding agent is used for bonding. An alternative embodiment employs a biocompatible agent or adhesive to facilitate bonding, such that the fibers are not self bonded, at least in part. Upon cooling, the assemblage of bonded fibers is sufficiently rigid and strong that the assemblage can be removed from the mold and handled. The bridge is sufficiently rigid that it can be implanted into a mammal where it facilitates the growth of blood vessels and delivery of blood flow to a blood-deficient site.

The orientation of the fibers in a lengthwise direction in the unbonded or self-bonded bridge provides lengthwise channels (or connected pores) among the fibers, which channels provide for uptake into the bridge of stem cells, growth factors, medicines, red blood cells and other bodily fluids and components carried in bodily fluids. The fibers are arranged to define channels within the bridge which facilitate fluid flow into and lengthwise within the bridge from one end to the other end. The orientation also provides for channels in a transverse direction generally perpendicular to the lengthwise direction of the oriented fibers, to facilitate uptake of fluids from the outer surface of the interior or core of the bridge. These longitudinal and transverse channels exert significant capillary forces on a liquid which cause the liquid to be drawn into the bridge. This capillary action facilitates the distribution of these fluids and components relatively uniformly through the bridge and enables fluids to flow from one end of the bridge to the other or to enter the bridge from its surface and transmit the liquid to its ends.

In one aspect the fibers of the vascular bridge are co-aligned fibers, in that at least about 75 or 85% by volume of the fibers in the bridge are longitudinally co-aligned. In this regard the fibers are co-aligned longitudinally, where "co-aligned longitudinally" and the like phrases (e.g., "in lengthwise co-alignment") as applied to a group of adjacent, bundled, or joined fibers in this application means that the alignment of each fiber in the group at any one place along at least about 75% of its length does not deviate more than about 25 degrees from parallel to the central axis of the bridge. In one preferred embodiment, each fiber in the group at any one place along at least about 75% of its length does not deviate more than about 15 degrees from parallel to the central axis of the bridge. In another preferred embodiment, each fiber in the group at any one place along at least about 75% of its length does not deviate more than about 10 degrees from the central axis of the bridge. So it is evident that this co-alignment aspect does not require 100% precise co-alignment of all fibers. The longitudinal co-alignment aspect also allows for some minor deviation of specific segments of individual fibers to an orientation outside these 25, 15, and 10 degree requirements. This is reflected in the requirement that the longitudinal co-alignment of each fiber along at least 75% of its length, rather than necessarily along its entire length. So up to about 25% of the length of an individual fiber may be misaligned because, for example, it was bent during the bridge-assembling process or otherwise. Each fiber in the bridge is not absolutely straight, nor is it lying along an absolutely straight line strictly parallel to all other fibers in the bridge. And each fiber is oriented generally in the same direction, but each is not oriented in exactly the same direction. Moreover, the bridge itself in certain embodiments is curved, bent, or otherwise not straight, in which cases the central axis of the bridge to which the alignment of the fibers is within 25 degrees of parallel is also curved, bent, or otherwise not straight. In certain embodiments a straight or curved bridge is machined into a more complex shape, in which instance the bridge central axis refers to the central axis as molded and prior to machining.

In order to allow capillary action and channel-forming, the bridge theoretically contains at least five fibers, although the bridge may contain up to several thousand individual fibers, depending upon the fiber diameter and the overall size of the vascular bridge. The fibers lie generally lengthwise of the bridge central axis (i.e., lie generally in the direction of the central axis) and are generally free of helical orientation about the bridge central axis. This arrangement applies to at least about 75 vol % of the fibers and preferably to substantially all of the fibers.

The aspect of this embodiment that the fibers are co-aligned longitudinally contemplates that the fibers are positioned so that they have a similar alignment, which similar alignment may be straight, bent, or curved. In most embodiments they are non-helical. In a separate and distinct aspect of certain preferred embodiments, this common alignment is limited to a generally straight alignment along at least about 75%, 85%, or 95% of the length of the fibers. In other words, at least about 75%, 85%, or 95% of each fiber is generally straight, i.e., at least about 75%, 85%, or 95% of the length of each fiber has an alignment which is within 10 degrees of a mean straight central axis for the fiber. So up to 5%, 15%, or 25% of the length of each fiber may be curved, bent, or otherwise deviate more than 10 degrees from straight in relation to the overall fiber length, but the rest of each fiber is generally straight in that it so deviates less than 10 degrees. In one preferred embodiment, substantially the entire length of each fiber is generally straight in that it deviates less than 10 degrees from the fiber's average central axis. The "mean straight central axis" is the imaginary central axis for the fiber which is absolutely straight and is an average of all axes along the fiber length.

In one embodiment, the fiber length is selected so that all, substantially all, or at least about 85 volume % of the individual fibers extend the entire length of the bridge. The fibers may be selected to have a pre-assembled length which corresponds to the length of the bridge. Or the length of the fibers may initially be longer than the desired ultimate bridge length, and the bridge is cut to the desired length. In an alternative embodiment, the length of a substantial portion (e.g., at least 40 vol %) or all of the fibers is significantly less than the entire length of the bridge.

The biocompatible material may be glassy, glass ceramic, or ceramic in nature. However the glassy state is preferred in this invention because, generally speaking, glassy materials are stronger and more chemically homogeneous than their crystalline or partially crystalline counterparts of the same composition. In this description, the term "glass" is used to include materials which are entirely glassy as well as materials which are part glassy and part crystalline. It is therefore preferable that the biocompatible material is substantially glass in that less than about 5 wt %, more preferable less than 1 wt %, of the component material is crystalline material. The fibers used in many embodiments of the invention, consistent with the foregoing description, are at least 99 wt % an amorphous or non-crystalline solid, for example made by fusing a mixture of oxides such as one or more of $SiO_2$, $B_2O_3$, $P_2O_5$ (known as glass forming oxides) with basic oxides such as the alkali and alkaline earth oxides, along with the optional one or more trace element compounds such as Cu compounds. In an alternative embodiment, the fibers include glass ceramics fibers that contain both glassy and crystalline regions which in many respects function in the same manner as a fiber that is completely (100%) non-crystalline. It is acceptable in some applications if the glass fiber crystallizes during an optional bonding step. The fibers may alternatively be pre-reacted biocompatible glasses such as glass fibers pre-reacted to have a thin surface layer of hydroxyapatite.

EXAMPLE 1

A vascular bridge was prepared from biocompatible, biodegradable glass fibers having a length of about 30 mm and a diameter of about 20 μm. The number of fibers was approximately 200, which were loosely assembled in to a bridge having a diameter of about 4000 μm. The composition of the glass was as follows:

| Glass | $SiO_2$ | $Na_2O$ | $P_2O_5$ | CaO | CuO | FeO | $CaF_2$ | $B_2O_3$ | ZnO | MnO | MgO |
|---|---|---|---|---|---|---|---|---|---|---|---|
| F | 44 | 25 | 6 | 20 | 0.2 | 0.2 | 1.0 | 2.2 | 0.6 | 0.2 | 0.6 |

The vascular bridge was implanted subcutaneously into the back of a rat as shown in FIG. 1. Prior to implantation, the bridges were washed twice with ethyl alcohol and heat sterilized at 250° C. for 2.5 hours in a small box furnace. For implantation, the back of the rat was shaved, sterilized with iodine, and washed with 70% ethanol. Each rat was anesthesized with a mixture of isofluorine and medical grade oxygen. Implantation was subcutaneously in a pocket formed in the back of each rat. Each pocket was sufficiently large to ensure that each scaffold could be inserted away from the incision site. The incisions were closed with super glue (Krazy® Glue, Elmers Products inc. Columbus, Ohio). After implantation, 0.1 mL of Penicillin G Procaine was injected into each thigh of the rat to prevent infection. The rats were placed on a heating pad in a cage with fresh air during recovery. The bridge was oriented perpendicular to the host's spine. FIG. 2 shows the vascular bridge upon removal from the host after two weeks. The darker areas indicate long sections of vessels generally aligned in the longitudinal direction of the fibers of the bridge. FIG. 3 is a magnified view of the bridge from FIGS. 1 and 2. Three separate areas of vascular growth varying in length from 2 mm to 4 mm are shown in the areas framed by the dashed lines.

EXAMPLE 2

A self-bonded vascular bridge was prepared from glass having the following composition:

| Glass | $SiO_2$ | $Na_2O$ | CaO | $K_2O$ | MgO | $P_2O_5$ |
|---|---|---|---|---|---|---|
| 13-93 | 53 | 6 | 20 | 12 | 5 | 4 |

Figure 4:
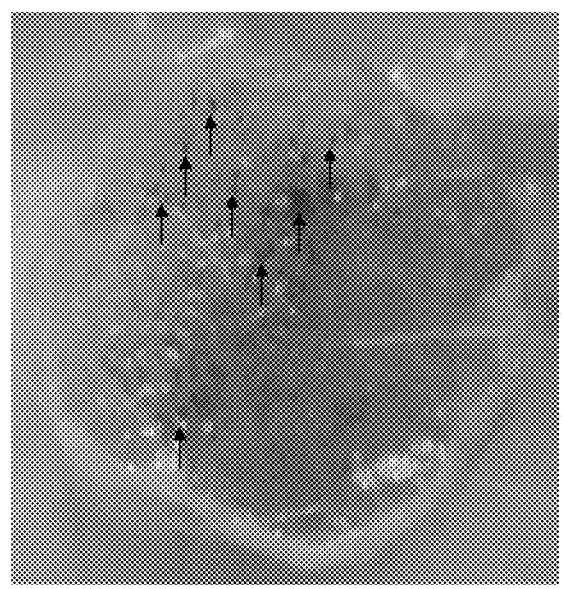
FIG. 4 is a photograph of a cross section of a vascular bridge of the invention after implantation and removal from a host.

The bridge was seeded with 50,000 mesenchymal stem cells (msc) and implanted subcutaneously into a rat. The bridge consisted of about 1000 fibers having a length of about 3000 μm and a diameter of about 200 μm. The overall bridge diameter was about 7000 μm. After six weeks, the bridge was removed for analysis, and a cross section prepared perpendicular to the longitudinal direction of the bridge. The photograph of FIG. 4 was taken, which shows several newly grown blood vessels at the surface of the cross section as indicated by arrows.

Figure 5:
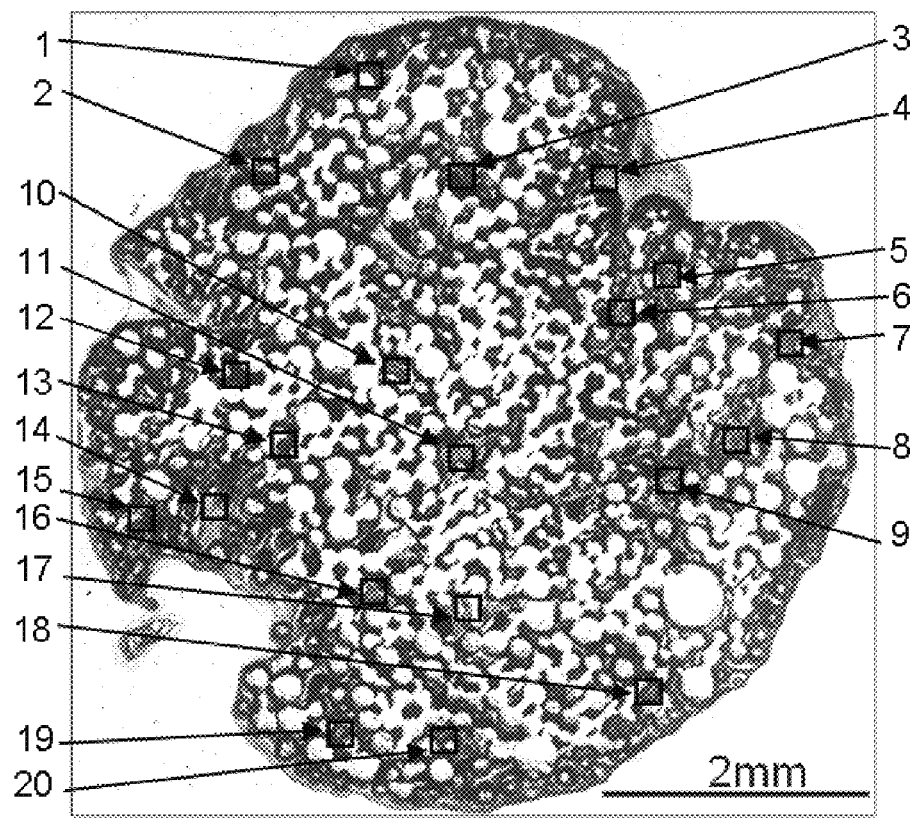
FIGS. 5 through 7 are photographs of a cross section of a vascular bridge of the invention after implantation and removal from a host, followed by staining for histology (H&E).
Figure 6:
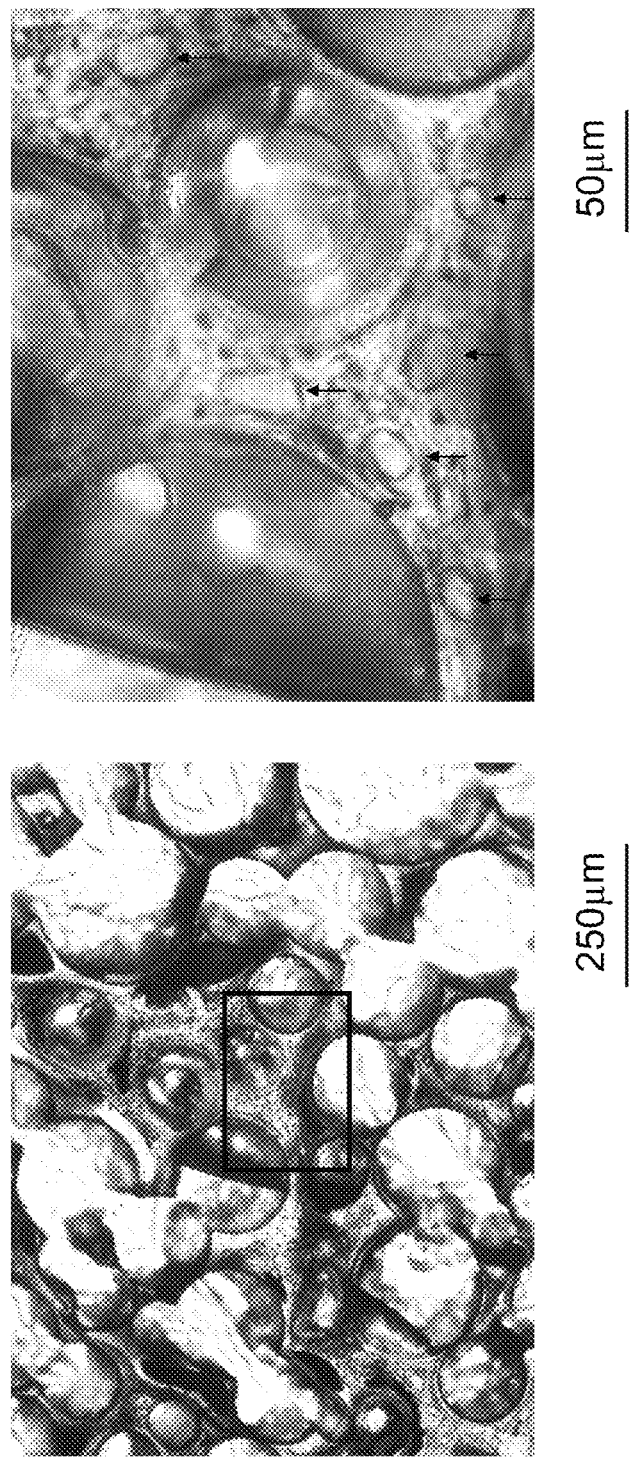
Figure 7:
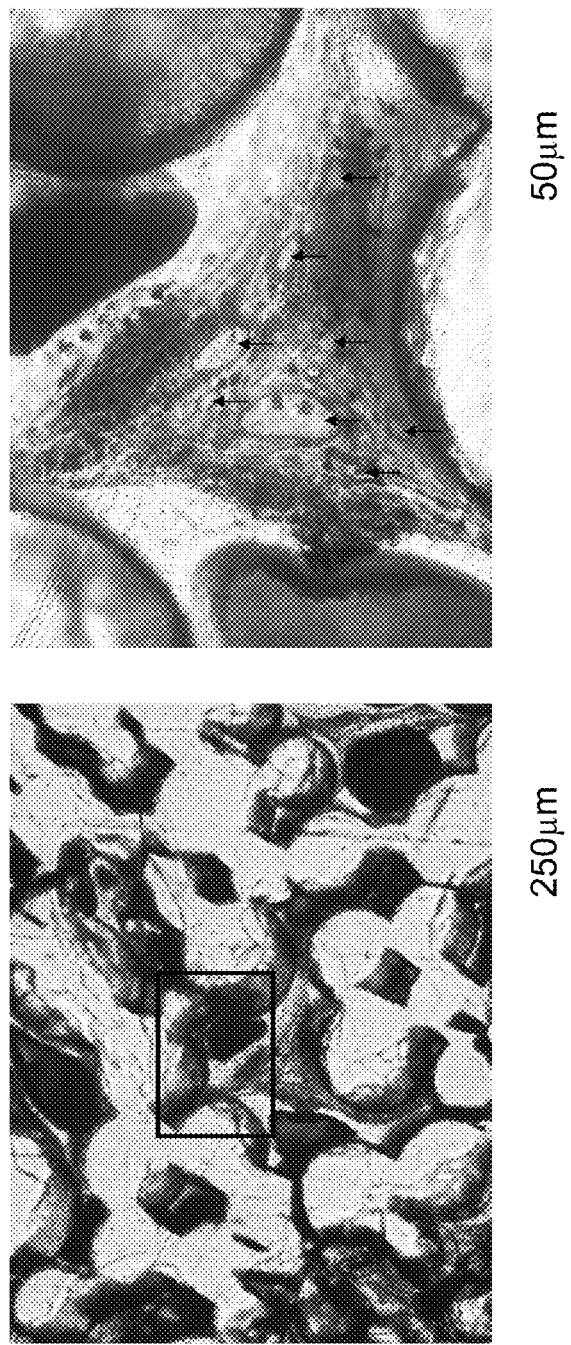
Figure 8:
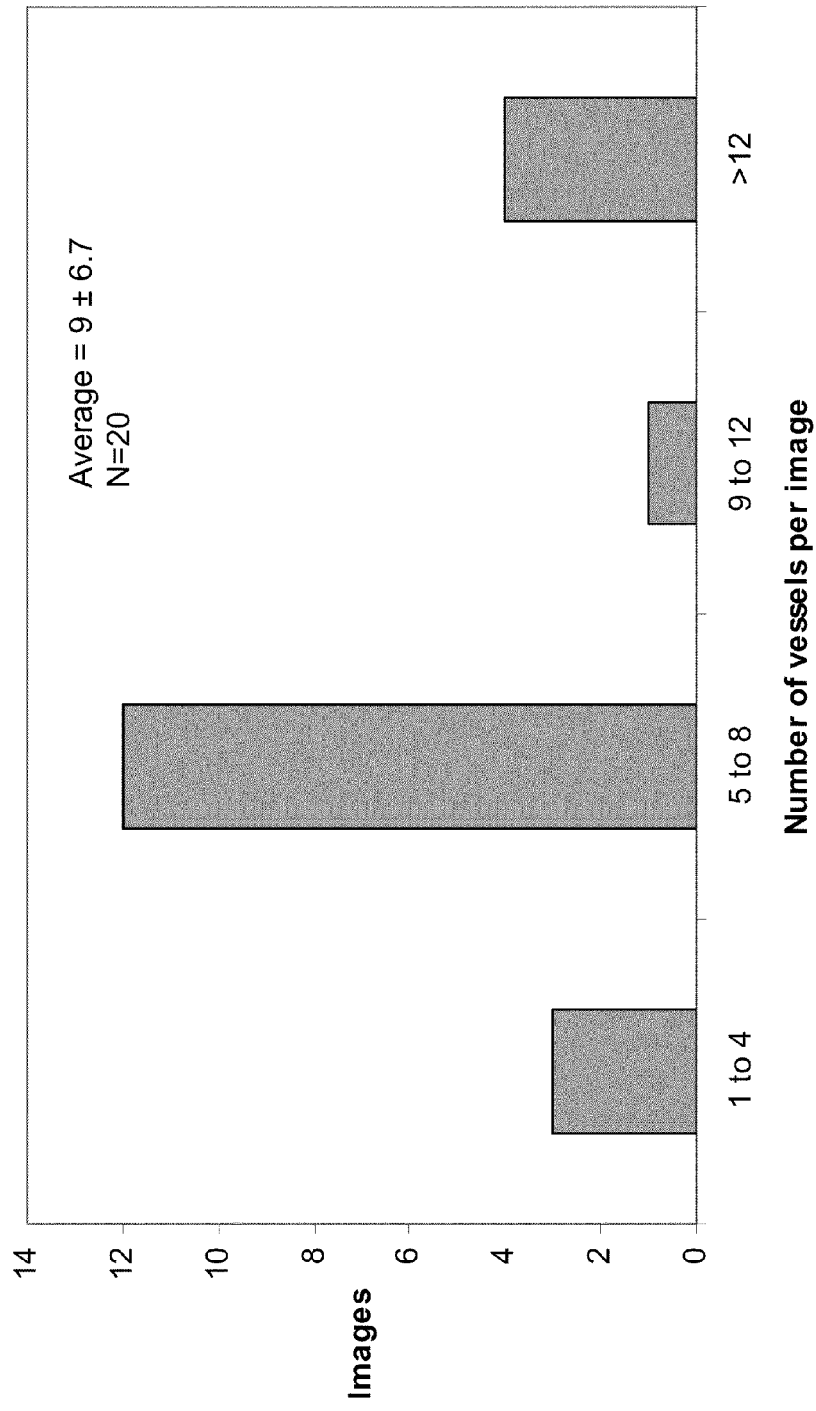
FIG. 8 is a graph illustrating the number of vessels grown in selected areas of the cross section of FIG. 5.

FIG. 5 is an image of the cross section after undergoing histological staining. Twenty areas (0.065 mm$^2$), denoted by the squares 1 through 20, were selected at random and the blood vessels in each box were counted. The average number of vessels per area (i.e., per box) was 9, +/−6.7. FIGS. 6 and 7 are photographs of areas 8 and 16, respectively, from FIG. 5, showing 6 vessels in area 8 and 8 vessels in area 16, with the individual vessels indicated by arrows. The right-side images in FIGS. 6 and 7 were taken from the boxes in the respective images from the left side of FIGS. 6 and 7. The graph in FIG. 8 is an analysis of the 20 areas, showing that three areas had 4 or less vessels, twelve areas had 5 to 8 vessels, one area had 9 to 12 vessels, and four areas had more than 12 vessels.

Figure 9:
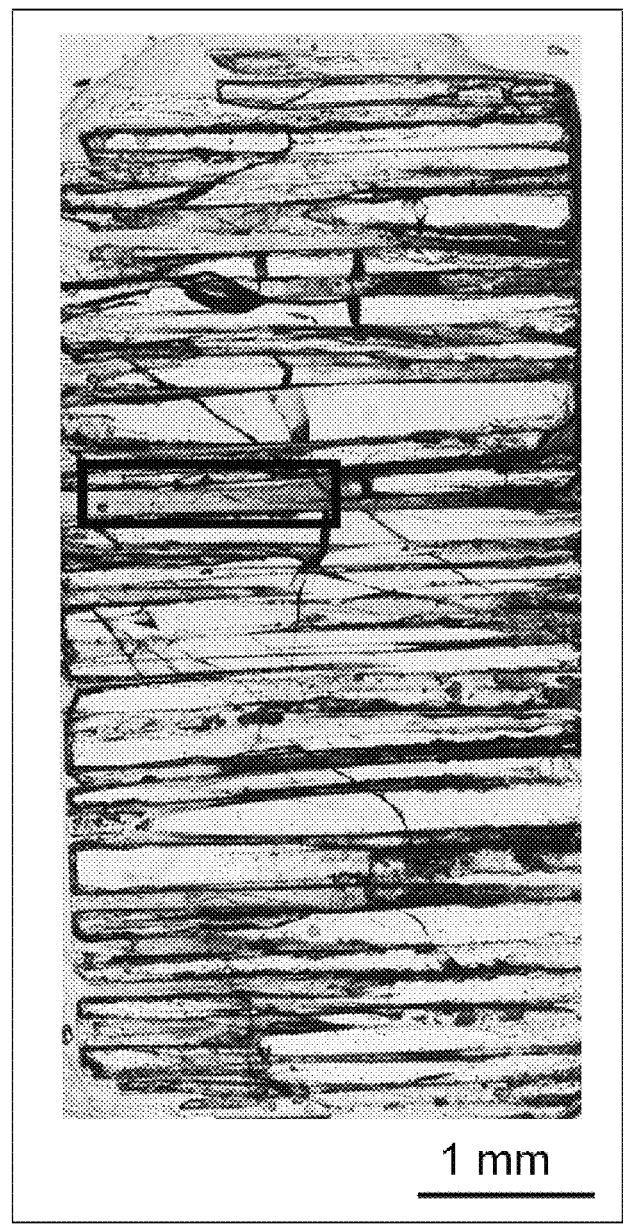
FIGS. 9 through 11 are photographs of a longitudinal cross section of a vascular bridge of the invention after implantation and removal from a host, followed by staining for histology (H&E).
Figure 10:
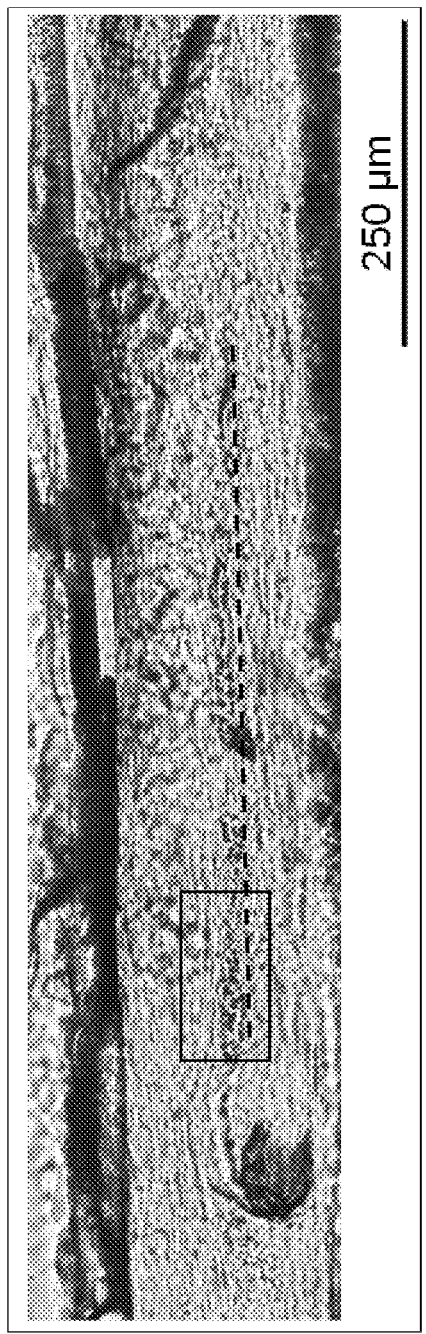
Figure 11:
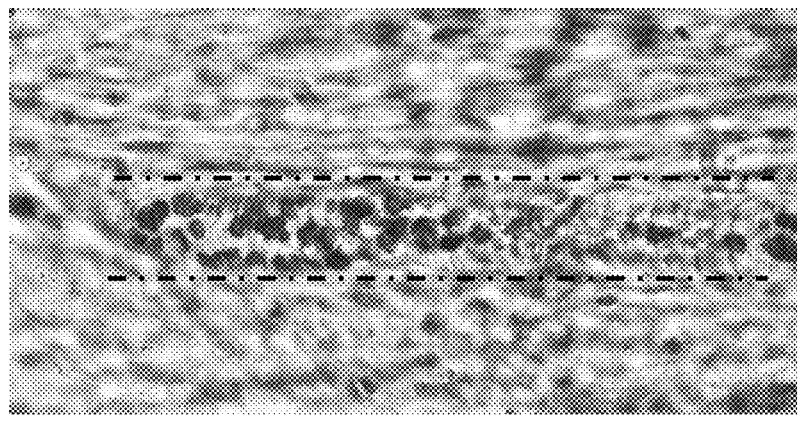

The same bridge after six-week implantation and removal was sectioned parallel to the longitudinal direction of the bridge, and the photograph of FIG. 9 was taken. FIG. 9 shows an area in a box which was evaluated at greater magnification in FIGS. 10 and 11. The area in the box in FIG. 9 is depicted in FIG. 10, and shows a blood vessel of about 600 microns in length in the longitudinal direction of the bridge, above the dashed line. FIG. 11 shows the area in the box in FIG. 10, with dark circles clearly showing red blood cells.

EXAMPLE 3

A vascular bridge was prepared from biocompatible, biodegradable solid self-bonded glass fibers having a length of about 3 mm and a diameter of about 100 to about 300 μm. The number of fibers was approximately 1000. The composition of the glass material was as follows:

| $B_2O_3$ | CaO | $Na_2O$ | $P_2O_5$ | $K_2O$ | MgO |
|---|---|---|---|---|---|
| 53 | 20 | 6 | 4 | 12 | 5 |

Figure 12:
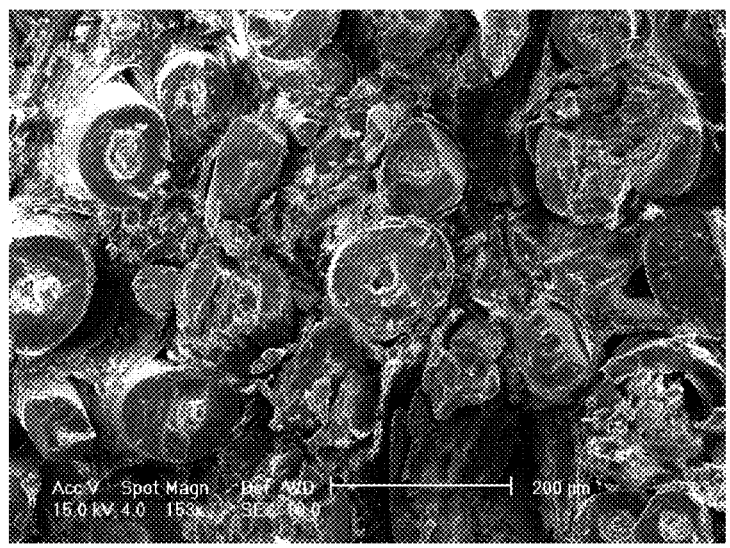
FIGS. 12 through 16 are micrographs of a vascular bridge analysis according to Example 3.
Figure 12:
Figure 13:
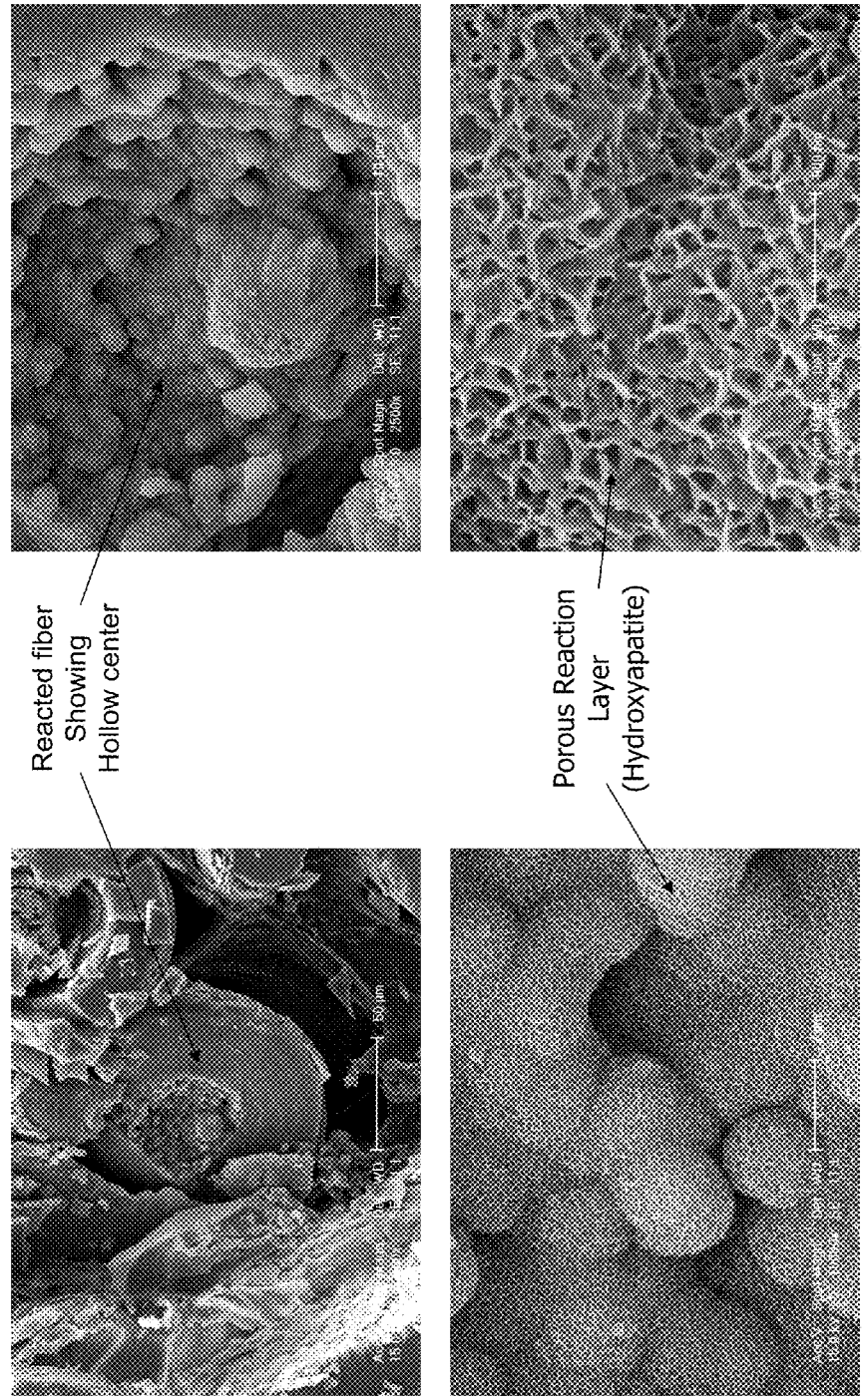

This bridge was implanted into a rat according to the protocol of Example 1. After 4 weeks in a subcutaneous site, the rat was sacrificed and the bridge evaluated as shown in FIGS. 12 through 16. FIG. 12 shows SEM micrographs of reacted fibers after four weeks subcutaneously implantation. Reacted fibers are completely surrounded by soft tissue. The dark gray areas depict soft tissue, and the lighter gray circular regions are the cross section of the fibers which have reacted to form a hollow core. Higher magnification SEM micrographs are shown in FIG. 13. The lower left view is of the nodules seen in the upper right view. The lower right view is a higher magnification micrograph of one of the nodules. This demonstrates a unique aspect of this invention in that when fibers of this bioactive glass come in contact with natural body fluids, they react to form a new biologically compatible material of different composition, typically hydroxyapatite, whose ideal composition is $Ca_{10}(PO_4)_6(OH)_2$, and in the process the fibers become hollow as shown in FIGS. 12 and 13. Hydroxyapatite is the inorganic component of human bone, so it is biologically compatible with living tissue.

Figure 14:
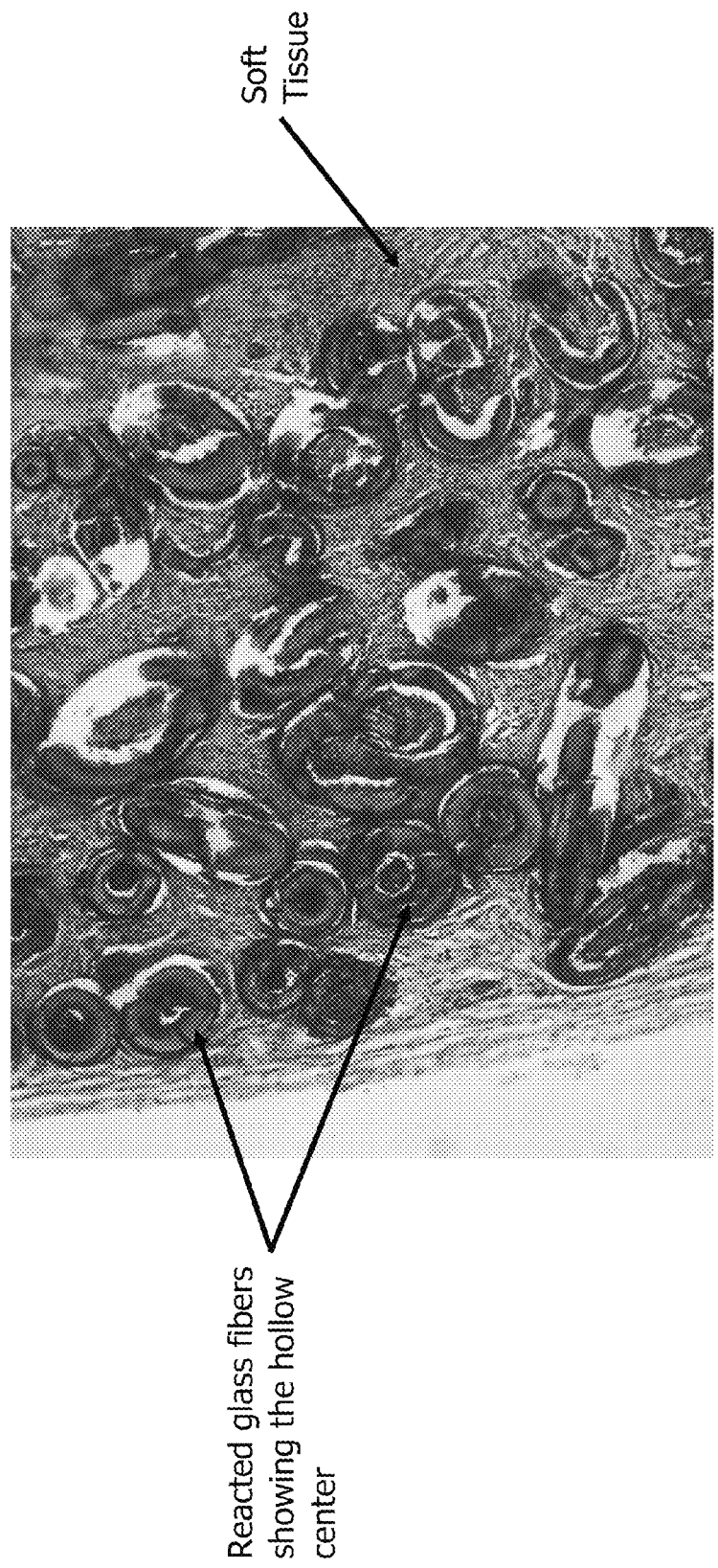
Figure 15:
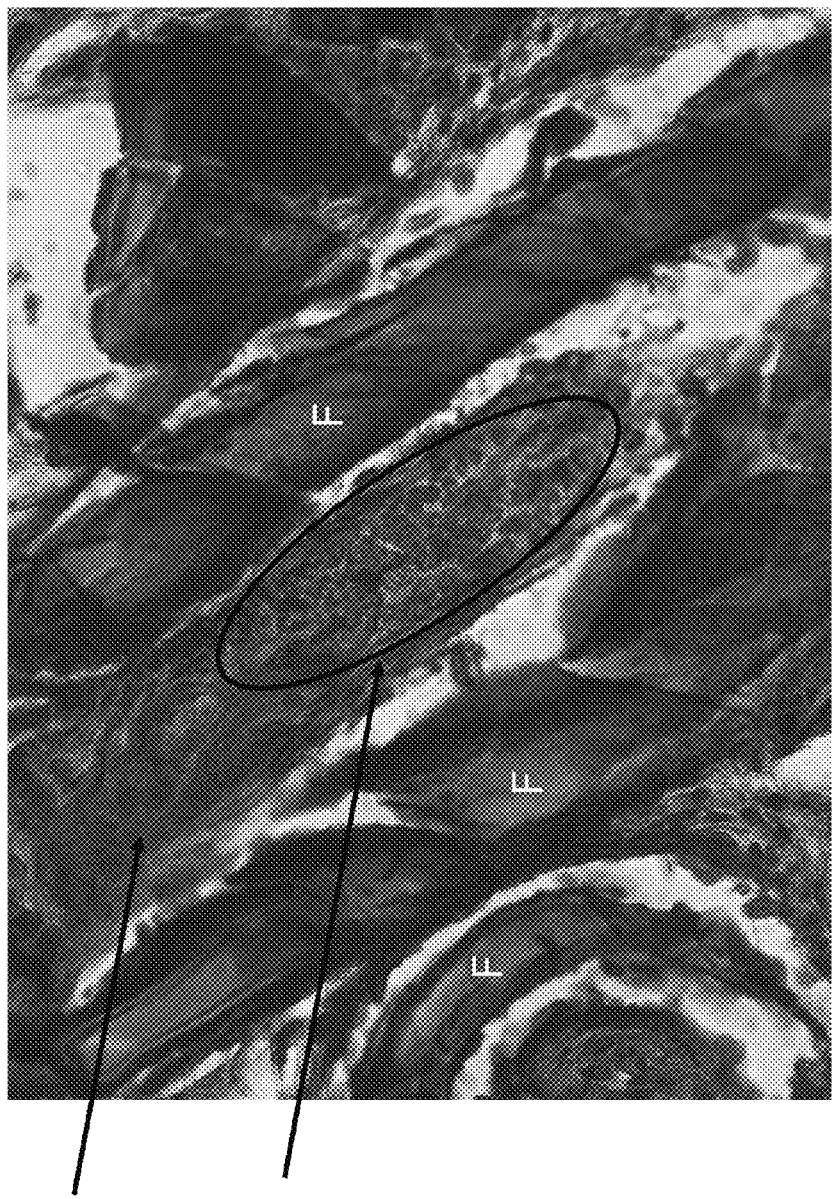
Figure 16:
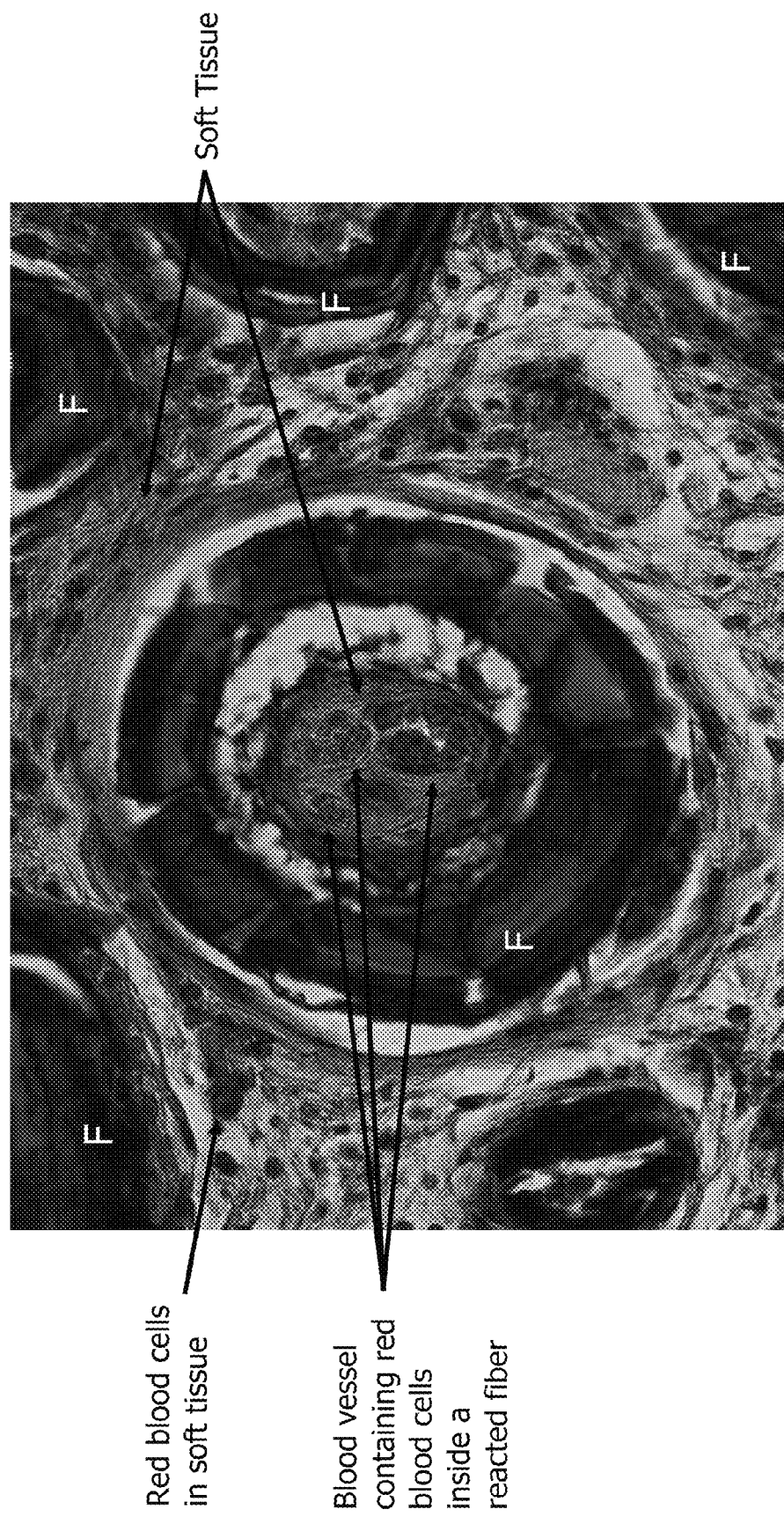

As shown in FIGS. 14 through 16, the fibers are surrounded by new tissue. FIG. 14 is an H&E stained section of the vascular bridge after removal from the rat. FIG. 15 is an H&E stained section of a cross section of a hollow fiber taken parallel to fiber longitudinal axis in which soft tissue and blood vessels had grown in and around the fiber. Walls of reacted fibers are shown at F in FIGS. 15 and 16. FIG. 16 is a cross section of a hollow fiber taken perpendicular to its longitudinal axis showing soft tissue and blood vessels growing inside and around the fiber. In FIG. 16, at least three separate vessels are present inside the fiber, indicating that multiple blood vessels can grow inside a single hollow fiber. The blood vessels again appear to have grown in the longitudinal direction of the hollow fiber. There are significant amounts of soft tissue surrounding the hollow fiber as well as areas of visible blood cells and vascular growth. These figures demonstrate a correlation between the directional growth of blood vessels, and other tissues of interest, and the orientation of the fibers in a specific direction of the vascular bridge. This is beneficial to controlling the direction of blood vessel growth for improving blood flow to areas of the body which are deficient (such as extremities of diabetics or burn patients), and guided nerve generation and regeneration. This correlation could also be beneficial to directional bone growth, especially cortical bone which is highly directionalized. This example demonstrates a vascular bridge comprising fibers of a calcium-containing biocompatible glass which upon dissolution in physiological fluids leaves a track comprising a calcium-containing compound from a second end of the bridge to a first end to support blood vessel growth from the second end to the first end.

In view of the above, it will be seen that the several objects of the invention are achieved and other advantageous results attained.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compositions and methods without departing from the scope of the invention, it is intended that all matter contained in the above description and shown in the accompanying drawings shall be interpreted as illustrative and not in a limiting sense.

The invention claimed is:

1. A method for directing vessel growth toward a blood-deficient site in a mammal comprising:
   implanting into the mammal an assembly comprising at least about 5 individual glass fibers to form a vascular bridge with a first end of the vascular bridge in contact with the blood-deficient site and a second end of the vascular bridge remote from the blood-deficient site and proximate a blood-rich site, such that the vascular bridge directs vessel growth to the blood-deficient site;
   wherein each of said at least about 5 individual glass fibers has a diameter which is between about 20 μm and about 450 μm and a length:diameter aspect ratio of greater than 10:1;
   wherein the length from the first end of the vascular bridge to the second end of the vascular bridge is at least about 1 millimeter;
   wherein an aspect ratio of the length to cross section of the bridge at least about 7.5:1;
   wherein said at least about 5 individual glass fibers are biocompatible glass fibers which biodegrade in physiological fluids and comprise at least one glass-former selected from the group consisting of $P_2O_5$, $SiO_2$, $B_2O_3$, and combinations thereof.

2. The method of claim 1 wherein the length of the vascular bridge is at least about 3 millimeters.

3. The method of claim 1 wherein the vascular bridge comprises between about 10 and about 10000 fibers each having a length of between about 3 and about 1000 millimeters.

4. The method of claim 1 wherein the vascular bridge comprises between about 10 and about 1000 fibers each having a length of between about 3 and about 50 millimeters.

5. The method of claim 1 wherein the vascular bridge comprises between about 50 and about 500 fibers each having a length of between about 3 and about 150 millimeters.

6. The method of claim 1 wherein the vascular bridge comprises between about 50 and about 500 fibers each having a length of between about 3 and about 50 millimeters.

7. The method of claim 1 wherein said fibers comprise borate-based glass.

8. The method of claim 1 wherein said fibers comprise a calcium-containing biocompatible glass which upon dissolution in physiological fluids leaves a track comprising a calcium-containing compound from said second end to said first end to support blood vessel growth from said second end to said first end.

9. The method of claim 1 wherein said vascular bridge upon dissolution in physiological fluids leaves a track comprising a porous hollow tube from said second end to said first end to support blood vessel growth from said second end to said first end.

10. The method of claim 1 wherein the fibers comprise one or more trace elements from the group consisting of Cu, F, Fe, Mn, Mo, Ni, Sr, and Zn in a concentration between about 0.05 and 10 wt % per trace element chemically dissolved in the biocompatible glass fibers.

11. The method of claim 1 wherein the fibers comprise one or more trace elements from the group consisting of Cu, Fe, Sr, and Zn in a concentration between about 0.05 and 10 wt % per trace element chemically dissolved in the biocompatible glass fibers.

12. The method of claim 1 wherein the fibers comprise Cu in a concentration between about 0.05 and 10 wt %.

13. The method of claim 1 wherein the glass fibers comprise no more than 5 wt % crystalline material.

14. The method of claim 1 wherein the glass fibers comprise a reacted surface layer.

15. The method of claim 14 wherein the reacted surface layer is a hydroxyapatite layer.

16. The method of claim 1 wherein the vascular bridge comprises fibers of a first composition and fibers of a second composition different from the first composition.

17. The method of claim 1 wherein the vascular bridge comprises a mixture of fibers of more than two distinct compositions.

18. The method of claim 1 wherein the vascular bridge further comprises glass particles.

19. The method of claim 1 wherein the vascular bridge further comprises glass of one or more non-fibrous morphologies selected from the group consisting of beads, particles, ribbons, hollow spheres, and flakes.

20. The method of claim 1 wherein the biocompatible glass fibers comprise from 40 to 80 wt % $B_2O_3$ and any $SiO_2$ is present in an amount only up to 18 wt %.

21. The method of claim 1 wherein the blood-deficient site is soft tissue selected from the group consisting of wounds, ulcers, sores, and severe burns.

22. The method of claim 1 wherein upon implantation the fibers biodegrade to form hollow fibers with blood vessels grown within the interior of hollow fibers in the longitudinal direction of the hollow fibers.

23. The method of claim 1 wherein:
   the blood-deficient site is soft tissue selected from the group consisting of wounds, ulcers, sores, and severe burns;
   the biocompatible glass fibers comprise from 40 to 80 wt % $B_2O_3$ and any $SiO_2$ is present in an amount only up to 18 wt %; and
   upon implantation the fibers biodegrade to form hollow fibers with blood vessels grown within the hollow fibers in the longitudinal direction of the hollow fibers.

24. The method of claim 1 wherein the biocompatible glass fibers contain less than 0.1 wt % silicate.

25. The method of claim 1 wherein the vascular bridge is a loose unbonded assemblage of said fibers.

26. The method of claim 1 wherein the vascular bridge consists of said fibers.

27. The method of claim 1 wherein each fiber of said at least about 5 individual glass fibers has a diameter which is between about 20 μm and about 50 μm.

28. The method of claim 1 wherein each fiber of said at least about 5 individual glass fibers has a diameter which is between about 50 μm and about 450 μm.

29. The method of claim 1 wherein the biocompatible glass fibers comprise from 40 to 80 wt % $B_2O_3$, one or more alkali oxide from the group consisting of $Li_2O$, $Na_2O$, $K_2O$, and $Rb_2O$ in a cumulative concentration between about 1 and about 50 wt %, and one or more alkaline earth oxide from the group consisting of MgO, SrO, BaO, and CaO in a cumulative concentration between about 1 and about 50 wt %.

30. The method of claim 1 wherein the biocompatible glass fibers comprise from 40 to 80 wt % $B_2O_3$, at least two alkali oxides from the group consisting of $Li_2O$, $Na_2O$, $K_2O$, and $Rb_2O$ in a cumulative concentration of between about 5 and about 25 wt %, and at least two alkaline earth oxides from the group consisting of MgO, SrO, BaO, and CaO in a cumulative concentration between about 5 to about 25 wt %.

31. The method of claim 1 wherein the biocompatible glass fibers comprise from 20 to 60 wt % $SiO_2$, one or more oxide from the group consisting of $Li_2O$, $Na_2O$, $K_2O$, $Rb_2O$, and $Cs_2O$ in a cumulative concentration between about 8 and about 55 wt %.

32. The method of claim 31 wherein the fibers further comprise about 5 wt % to about 40 wt % of CaO or $CaF_2$ or mixtures thereof.

33. A method for directing vessel growth toward a blood-deficient site in a mammal comprising:
 implanting into the mammal an assembly comprising at least about 5 individual glass fibers to form a vascular bridge with a first end of the vascular bridge in contact with the blood-deficient site and a second end of the vascular bridge remote from the blood-deficient site and proximate a blood-rich site, such that the vascular bridge directs vessel growth to the blood-deficient site;
 wherein each fiber of said at least about 5 individual glass fibers has a length:diameter aspect ratio of greater than 10:1;
 wherein the length from the first end of the vascular bridge to the second end of the vascular bridge is at least about 1 millimeter;
 wherein an aspect ratio of the length to cross section of the bridge at least about 7.5:1:
 wherein said at least about 5 individual glass fibers are biocompatible glass fibers which biodegrade in physiological fluids and comprise at least one glass-former selected from the group consisting of $P_2O_5$, $SiO_2$, $B_2O_3$, and combinations thereof;
 wherein the at least about 5 individual glass fibers are melt-derived fibers.

* * * * *

UNITED STATES PATENT AND TRADEMARK OFFICE
CERTIFICATE OF CORRECTION

PATENT NO.        : 8,337,875 B2                          Page 1 of 1
APPLICATION NO.   : 12/683211
DATED             : December 25, 2012
INVENTOR(S)       : Steven B. Jung and Delbert E. Day It is certified that error appears in the above-identified patent and that said Letters Patent is hereby corrected as shown below:

In the Specification

Column 1, line 13: "W81XWH-08-1-7065" should read -- W81XWH-08-1-0765 --.

Signed and Sealed this
Twenty-first Day of April, 2015

Michelle K. Lee
*Director of the United States Patent and Trademark Office*